(12) United States Patent
Rossi et al.

(10) Patent No.: US 9,365,849 B2
(45) Date of Patent: Jun. 14, 2016

(54) METHODS AND COMPOSITIONS FOR THE SPECIFIC INHIBITION OF GENE EXPRESSION BY DOUBLE-STRANDED RNA

(71) Applicants: CITY OF HOPE, Duarte, CA (US); INTEGRATED DNA TECHNOLOGIES, INC., Coralville, IA (US)

(72) Inventors: John J. Rossi, Alta Loma, CA (US); Mark A. Behlke, Coralville, IA (US); Dongho Kim, Los Angeles, CA (US)

(73) Assignees: Integrated DNA Technologies, Inc., Coralville, IA (US); City of Hope, Duarte, CA (US)

( * ) Notice: Subject to any disclaimer, the term of this patent is extended or adjusted under 35 U.S.C. 154(b) by 0 days.

(21) Appl. No.: 14/019,911

(22) Filed: Sep. 6, 2013

(65) Prior Publication Data

US 2013/0345291 A1    Dec. 26, 2013

Related U.S. Application Data

(63) Continuation of application No. 13/178,844, filed on Jul. 8, 2011, now abandoned, which is a continuation of application No. 12/855,223, filed on Aug. 12, 2010, now abandoned, which is a continuation of application No. 11/079,476, filed on Mar. 15, 2005, now abandoned.

(60) Provisional application No. 60/553,487, filed on Mar. 15, 2004.

(51) Int. Cl.
    *C07H 21/04*      (2006.01)
    *C12N 15/113*     (2010.01)
    *C12N 15/11*      (2006.01)

(52) U.S. Cl.
    CPC ............ *C12N 15/113* (2013.01); *C12N 15/111* (2013.01); *C12N 2310/14* (2013.01); *C12N 2310/33* (2013.01); *C12N 2310/51* (2013.01); *C12N 2320/30* (2013.01); *C12N 2320/51* (2013.01); *C12N 2330/30* (2013.01)

(58) Field of Classification Search
    None
    See application file for complete search history.

(56) References Cited

U.S. PATENT DOCUMENTS

| | | |
|---|---|---|
| 5,624,803 A | 4/1997 | Noonberg et al. |
| 5,898,031 A | 4/1999 | Crooke |
| 6,107,094 A | 8/2000 | Crooke |
| 2002/0086356 A1 | 7/2002 | Tuschl et al. |
| 2002/0114784 A1 | 8/2002 | Li et al. |
| 2003/0108923 A1 | 6/2003 | Tuschl et al. |
| 2003/0206887 A1 | 11/2003 | Morrissey et al. |
| 2004/0014956 A1 | 1/2004 | Woolf et al. |
| 2004/0018176 A1* | 1/2004 | Tolentino et al. .......... 424/93.21 |
| 2004/0023390 A1 | 2/2004 | Davidson et al. |
| 2004/0147476 A1 | 7/2004 | Satishchandran et al. |
| 2004/0152117 A1 | 8/2004 | Giordano et al. |
| 2004/0180438 A1 | 9/2004 | Pachuk |
| 2004/0192626 A1 | 9/2004 | McSwiggen et al. |
| 2004/0203145 A1 | 10/2004 | Zamore et al. |
| 2004/0224405 A1 | 11/2004 | Leake et al. |
| 2004/0248299 A1 | 12/2004 | Jayasena et al. |
| 2004/0259247 A1 | 12/2004 | Tuschl et al. |
| 2005/0020525 A1 | 1/2005 | McSwiggen et al. |
| 2005/0032733 A1 | 2/2005 | McSwiggen et al. |
| 2005/0039224 A1 | 2/2005 | Pachuk et al. |
| 2005/0042646 A1 | 2/2005 | Davidson et al. |
| 2005/0186586 A1 | 8/2005 | Zamore et al. |
| 2005/0233329 A1 | 10/2005 | McSwiggen et al. |
| 2005/0239728 A1 | 10/2005 | Pachuk et al. |
| 2005/0244858 A1 | 11/2005 | Rossi et al. |
| 2005/0282188 A1 | 12/2005 | Haeberli et al. |
| 2006/0009402 A1 | 1/2006 | Zamore et al. |
| 2006/0009409 A1 | 1/2006 | Woolf |
| 2007/0265220 A1 | 11/2007 | Rossi et al. |
| 2008/0146788 A1 | 6/2008 | Bhat et al. |
| 2009/0018321 A1 | 1/2009 | Rossi et al. |
| 2009/0029466 A1 | 1/2009 | Rossi et al. |
| 2009/0029936 A1 | 1/2009 | Rossi et al. |

(Continued)

FOREIGN PATENT DOCUMENTS

| | | |
|---|---|---|
| WO | 0104313 A1 | 1/2001 |
| WO | WO 02/44321 A2 | 6/2002 |

(Continued)

OTHER PUBLICATIONS

Holen et al. (Nucleic Acids Research 2002, vol. 30: 1757-1766).*
JP Appln No. 2007-504009, English translation of Office Action issued on Aug. 9, 2012, 5 pages.
WO 2005/063630 (Jul. 28, 2005) with excerpt translation, 78 pages.
Elbashir S.M., "Functional anatomy of siRNAs for mediating efficient RNAi in *Drosophila melanogaster* embryo lysate," The EMBO Journal, vol. 20, No. 23, pp. 6877-6888, 2001.
Tuschl, T. et al., "Small interfering RNAs: A revolutionary tool for the analysis of gene function and gene therapy," Molecular Interventions, American Society for Pharmacology and Experimental Therapeutics, Bethesda, MD, US, vol. 2, No. 3, Jun. 2002, pp. 158-167.

(Continued)

*Primary Examiner* — Kimberly Chong
(74) *Attorney, Agent, or Firm* — Rothwell, Figg, Ernst & Manbeck P.C.

(57) ABSTRACT

The invention provides compositions and methods for selectively reducing the expression of a gene product from a desired target gene, as well as treating diseases caused by expression of the gene. The method involves introducing into the environment of a cell an amount of a double-stranded RNA (dsRNA) such that a sufficient portion of the dsRNA can enter the cytoplasm of the cell to cause a reduction in the expression of the target gene. The dsRNA has a first oligonucleotide sequence that is between 26 and about 30 nucleotides in length and a second oligonucleotide sequence that anneals to the first sequence under biological conditions. In addition, a region of one of the sequences of the dsRNA having a sequence length of from about 19 to about 23 nucleotides is complementary to a nucleotide sequence of the RNA produced from the target gene.

23 Claims, 13 Drawing Sheets

(56) References Cited

U.S. PATENT DOCUMENTS

| | | | |
|---|---|---|---|
| 2009/0035854 A1 | 2/2009 | Rossi et al. | |
| 2009/0036661 A1 | 2/2009 | Rossi et al. | |
| 2009/0043083 A1 | 2/2009 | Rossi et al. | |
| 2009/0043085 A1 | 2/2009 | Rossi et al. | |
| 2009/0325181 A1 | 12/2009 | Rossi et al. | |
| 2009/0325285 A1 | 12/2009 | Rossi et al. | |
| 2009/0325286 A1 | 12/2009 | Rossi et al. | |
| 2009/0326046 A1 | 12/2009 | Rossi et al. | |
| 2010/0003758 A1 | 1/2010 | Rossi et al. | |
| 2010/0004317 A1 | 1/2010 | Rossi et al. | |
| 2010/0004318 A1 | 1/2010 | Rossi et al. | |
| 2010/0004434 A1 | 1/2010 | Rossi et al. | |
| 2010/0004435 A1 | 1/2010 | Rossi et al. | |
| 2010/0004436 A1 | 1/2010 | Rossi et al. | |
| 2010/0069465 A1 | 3/2010 | Rossi et al. | |

FOREIGN PATENT DOCUMENTS

| | | | |
|---|---|---|---|
| WO | 02/055693 A2 | 7/2002 | |
| WO | 03/079757 A2 | 10/2003 | |
| WO | 2004011647 A1 | 2/2004 | |
| WO | 2004029215 A2 | 4/2004 | |
| WO | 2004035765 A2 | 4/2004 | |
| WO | 2004076629 A2 | 9/2004 | |
| WO | 2005014806 A2 | 2/2005 | |
| WO | WO 2005/019453 A2 | 3/2005 | |
| WO | 2005040388 A2 | 5/2005 | |
| WO | 2005/120230 A2 | 12/2005 | |

OTHER PUBLICATIONS

European Search Report dated Sep. 21, 2012; Reference: OWK/G28594EP-D1, Application No./Patent No. 12174021.1-2405; Applicant: City of Hope, 7 pages.

Behlke, M.A., "Progress towards in vivo use of siRNAs," Mol Ther, 2006, 13(4):644-70.

Behlke, M.A., "27mer DNA duplexes as Triggers of RNAi," BIOforum Europe Jun. 2006: 25-27.

Massaro, D. et al., "Noninvasive delivery of small inhibitory RNA and other reagents to pulmonary alveoli in mice," Am J Physiol Lung Cell Mol Physiol, 2004, 267:L1066-1070.

Soutschek, J. et al.,"Therapeutic silencing of an endogenous gene by systemic administration of modified siRNAs," Nature, 2004, 432:173-178.

Thakker, D.R. et al., "Neurochemical and behavioral consequences of widespread gene knockdown in the adult mouse brain by using nonviral RNA interference," Proc Natl Acad Sci USA, 2004, 101:17270-17275.

Zhang, X. et al., "Small interfering RNA targeting heme oxygenase-1 enhances ischemia-reperfusion-induced lung apoptosis," J Biol Chem, 2004, 279:10677-10684.

Grunweller, et al., "Comparison of different antisense strategies in mammalina cells using locked nucleic acids, 2'-O-methyl RNA, phosphorothiates and small interfering RNA", (2003), pp. 3185-3193, vol. 31(12), Nucleic Acids Research.

Hannoush, et al., "Remarkable Stability of Hairpins Containing 2'-, 5'-linked RNA Loops", (2001), pp. 12368-12374, vol. 123(49), J. Am. Chem. Soc.

Paroo et al., "Challenges for RNAi in vivo," Trends in Biotechnology (2004), vol. 22(8) 390-394. Elsevier.

Caplen, NJ, "RNAi as a Gene Therapy Approach," Expert Opinion. Biol. Thera. (2003), vol. 3(4) 575-586, Ashley Publications, Ltd.

Adams, A., "RNA Therapeutics Enter Clinical Trials," Scientist (2005), vol. 19: Issue 1, Institute for Scientific Information.

Novina et al., "The RNAi Revolution," Nature 2004, vol. 430:161-164, Nature Publishing Group.

Zhang et al., "Human dicer preferentially cleaves dsRNAs at their termini without a requirement for ATP," EMBO 2002, vol. 21, No. 21:pp. 5875-5885.

Holen et al., (Nucleic Acids Research 2002, vol. 30: 1757-1766).

U.S. Appl. No. 06/506,559, filed Jan. 14, 2003, Fire et al.

Amarzguioul, M. et al., Tolerance for Mutations and Chemical Modifications in a siRNA, Nucleic Acids Research, vol. 31, 2003, pp. 589-595.

Bernstein, E., et al., "Role for a bidentate ribonuclease in the initiation step of RNA interference", Nature, vol. 409, (2001) pp. 363-366.

Caplen, N.J., et al., "Specific inhibition of gene expression by small souble-stranded RNAs in invertebrate and vertebrate systems," Proc. Nat'l Acad. Sci., USA, 2001, vol. 98, No. 17, pp. 9742-9747.

Elbashir, S.M., et al. "Duplexes of 21-nucleotide RNAs mediate RNA interference in cultured mammalian cells", Nature, vol. 411, (2011) pp. 494-498.

Elbashir, S.M., et al., "RNA interference is mediated by 21- and 22-nucleotide RNAs," Genes & Development, vol. 15, pp. 188-200, 2001.

Fire, Andrew, et al., "Potent and specific genetic interference by double-stranded RNA in Caenorhabditis elegans," Nature, Feb. 1998, vol. 391-806-811.

Harborth, J., et al., "Sequence, chemical, and structural variation of small interfering RNAs and short hairpin RNAs and the effect on mammalian gene silencing", Antisense Nucleic Acid Drug Dev., (2003), vol. 13, pp. 83-105.

Hemmings-Mieszczak, M., et al., "Independent combinatorial effect of antisense oligonucleotides and RNAi-mediated specific inhibitionof the recombinant rat P2X3 receptor", Nucleic Acids Res., Apr. 2003, vol. 31, No. 8, pp. 2117-2126.

Hohjoh, H., "RNA interference (RNAi) induction with various types of synthetic oligonucleotide duplexes in cultured human cells," FEBS Lett., (2002) vol. 521, pp. 195-199.

Kim, D.H., et al., Synthetic dsRNA Dicer substrates enhance RNAi potency and efficacy, Nat. Biotechnology, Feb. 2005, vol. 23, No. 2, pp. 222-226.

Khvorova, A., et al., "Functional siRNAs and miRNAs exhibit strand bias", Cell, vol. 115, Oct. 2003, pp. 209-216.

Krol, J. et al., "Structural features of microRNA (miRNA) precursors and their relevance to miRNA biogenesis and small interfering RNA/short hairpin RNA design", J. Biological Chemistry, Vo. 279, No. 40, Oct. 2004, pp. 42230-42239.

Martinez, J., et al., "Single-stranded antisense siRNAs guide target RNA cleavage in RNAi", Cell, 2002, vol. 110, pp. 563-574.

McManus, et al., "Gene Silencing in Mammals by Small Interfering RNAs", Nature Reviews Genetics, 2002, vol. 3, pp. 737-747.

Murchison, E.P. et al., "miRNAs on the move: miRNA biogenesis and the RNAi machinery", Curr. Opin. Cell Biology, Jun. 2004, vol. 16, No. 3, pp. 223-229.

Parrish, S., et al. , "Functional anatomy of a dsRNA trigger: differential requirement for the two trigger strands in RNA interference," Mol. Cell, (2000) vol. 6, pp. 1077-1087.

Paul, C., et al., "Effective expression of small interfering RNA in human cells," Nat. Biotech., May 2002, vol. 29, pp. 505-508.

Reynolds, et al., "Rational siRNA design for RNA interference," Nat. Biotechnol. (2004) vol. 22, pp. 326-330.

Scherer et al., "Approaches for the Sequence-Specific Knockdown of mRNA", Nature Biotechnology, 2003, vol. 21, No. 12, pp. 1457-1465.

Schwarz, D.S. et al., "Asymmetry in the assembly of the RNAi enzyme complex", Cell, 2003, vol. 115, pp. 119-208.

Siolas, D., et al., "Synthetic shRNAs as potent RNAi triggers", Nat. Biotechnology, Feb. 2005, vol. 23, No. 2, pp. 227-231.

Tuschl, T., "Expanding small RNA interference," Nat. Biotech., vol. 20, May 2002, pp. 446-448.

Ui-Tei, K.,et al., "Guidelines for the selection of highly effective siRNA sequences for mammalian and chick RNA interference", Nucleic Acids Res., (2004) vol. 32, pp. 936-948.

Vermeulen, A., et al., "The contributions of dsRNA structure of Dicer specificity and efficiency", RNA, May 2005, vol. 11, No. 5, pp. 674-682.

Williams, B., "Dicing with siRNA", Nature Biotech., vol. 23, No. 2, Feb. 2005, pp. 181-182.

Zamore, P.D., et al., "RNAi: double-stranded RNA directs the ATP-dependent cleavage of mRNA at 21 to 23 nucleotide intervals", Cell, (2000) vol. 101, pp. 25-33.

(56) References Cited

OTHER PUBLICATIONS

Non-Final Office Action dated Apr. 14, 2006, U.S. Appl. No. 11/079,906, filed Mar. 15, 2005: Response to Office Action dated Aug. 14, 2008, 51 pages.
Non-Final Office Action dated Dec. 1, 2008, U.S. Appl. No. 11/079,906, filed Mar. 15, 2005: Response to Office Action dated Jun. 1, 2009, 49 pages.
Final Office Action dated Sep. 18, 2009, U.S. Appl. No. 11/079,906, filed Mar. 15, 2005; Response to Office Action dated May 18, 2010, 53 pages.
Non-Final Office Action dated Nov. 19, 2007, U.S. Appl. No. 11/079,476, filed Mar. 15, 2005; Response to Office Action dated May 19, 2008, 24 pages.
Non-Final Office Action dated Sep. 5, 2008, U.S. Appl. No. 11/079,476, filed Mar. 15, 2005; Response to Office Action dated Feb. 5, 2009, 23 pages.
Supplemental Response to Office Action dated Apr. 16, 2009, 4 pages, U.S. Appl. No. 11/079,476, filed Mar. 15, 2005.
Final Office Action dated Jul. 15, 2009, U.S. Appl. No. 11/079,476, filed Mar. 15, 2005; Response to Office Action dated Jan. 15, 2010, 19 pages.
Advisory Action dated Feb. 19, 2010, U.S. Appl. No. 11/079,476, filed Mar. 15, 2005.
Non-Final Office Action dated Dec. 31, 2009, U.S. Appl. No. 11/797,216, filed May 1, 2007.
Non-Final Office Action dated Mar. 20, 2009, U.S. Appl. No. 12/137,914, filed Jun. 12, 2008; Response to Office Action dated Jul. 20, 2009, 19 pages.
Non-Final Office Action dated Mar. 19, 2009, U.S. Appl. No. 12/138,215, filed Jun. 12, 2008; Response to Office Action dated Jul. 20, 2009, 14 pages.
Final Office Action dated Apr. 30, 2010, U.S. Appl. No. 12/138,215, filed Jun. 12, 2008.
Non-Final Office Action dated Jun. 12, 2009, U.S. Appl. No. 12/143,002, filed Jun. 20, 2008; Response to Office Action dated Nov. 12, 2009, 21 pages.
Non-Final Office Action dated Jun. 19, 2009, U.S. Appl. No. 12/143,006, filed Jun. 20, 2008; Response to Office Action dated Oct. 16, 2009, 32 pages.
Non-Final Office Action dated Jun. 15, 2009, U.S. Appl. No. 12/143,009, filed Jun. 20, 2008; Response to Office Action dated Oct. 14, 2009, 24 pages.
Non-Final Office Action dated Jun. 10, 2009, U.S. Appl. No. 12/143,024, filed Jun. 20, 2008; Response to Office Action dated Oct. 13, 2009, 23 pages.
Non-Final Office Action dated Apr. 3, 2009, U.S. Appl. No. 12/143,027, filed Jun. 20, 2008; Response to Office Action dated Oct. 5, 2009, 20 pages.
European Office Action dated Nov. 24, 2014, EP Application No. 05 732 148.1, 5 pages.
European Office Action dated Nov. 24, 2014, EP Application No. 12 174 021.1, 5 pages.

\* cited by examiner

A.

B.

C.

D.

A.

B.

METHODS AND COMPOSITIONS FOR THE SPECIFIC INHIBITION OF GENE EXPRESSION BY DOUBLE-STRANDED RNA

CROSS-REFERENCE TO RELATED APPLICATION

The present application is a continuation of U.S. patent application Ser. No. 13/178,844, filed 8 Jul. 2011, which in turn is a continuation of U.S. patent application Ser. No. 12/855,223, filed 12 Aug. 2010, now abandoned, which in turn is a continuation of U.S. patent application Ser. No. 11/079,476 filed 15 Mar. 2005, now abandoned, which in turn is related to and claims priority under 35 U.S.C. §119(e) to U.S. provisional patent application No. 60/553,487 filed 15 Mar. 2004. Each application is incorporated herein by reference.

STATEMENT REGARDING FEDERALLY SPONSORED RESEARCH AND DEVELOPMENT

This invention was made in part with Government support under Grant Numbers AI29329 and HL074704 awarded by the National Institute of Health. The Government has certain rights in this invention.

SEQUENCE SUBMISSION

The present application is being filed along with a Sequence Listing in electronic format. The Sequence Listing is entitled 1954567SequenceListing.txt, was created on 26 Aug. 2013 and is 17 kb in size. The information in the electronic format of the Sequence Listing is incorporated herein by reference in its entirety.

FIELD OF THE INVENTION

This invention pertains to compositions and methods for gene-specific inhibition of gene expression by double-stranded ribonucleic acid (dsRNA) effector molecules. The compositions and methods are useful in modulating gene expression in a variety of applications, including therapeutic, diagnostic, target validation, and genomic discovery.

BACKGROUND OF THE INVENTION

Suppression gene expression by double-stranded RNA (dsRNA) has been demonstrated in a variety of systems including plants (post-transcriptional gene suppression) (Napoli et al., 1990, *Plant Cell.* 2:279-289), fungi (quelling) (Romano and Marcino, 1992, Mol Microbiol. 6:3343-53), and nematodes (RNA interference) (Fire et al., 1998, *Nature* 391:806-811). Early attempts to similarly suppress gene expression using long dsRNAs in mammalians systems failed due to activation of interferon pathways that do not exist in lower organisms. Interferon responses are triggered by dsRNAs (Stark et al., 1998, *Annu. Rev. Biochem.*, 67:227-264). In particular, the protein kinase PKR is activated by dsRNAs of greater than 30 bp long (Manche et al., 1992, *Mol Cell Biol.,* 12:5238-48) and results in phosphorylation of translation initiation factor eIF2α which leads to arrest of protein synthesis and activation of 2'5'-oligoadenylate synthetase (2'-5'-OAS), which leads to RNA degradation (Minks et al., 1979, *J. Biol. Chem.* 254:10180-10183).

In *Drosophila* cells and cell extracts, dsRNAs of 150 bp length or greater were seen to induce RNA interference while shorter dsRNAs were ineffective (Tuschl et al., 1999, *Genes & Dev.*, 13:3191-3197). Long double-stranded RNA, however, is not the active effecter molecule; long dsRNAs are degraded by an RNase III class enzyme called Dicer (Bernstein et al., 2001, *Nature*, 409:363-366) into very short 21-23 bp duplexes that have 2-base 3'-overhangs (Zamore et al., 2000, *Cell*, 101:25-33). These short RNA duplexes, called siRNAs, direct the RNAi response in vivo and transfection of short chemically synthesized siRNA duplexes of this design permits use of RNAi methods to suppress gene expression in mammalian cells without triggering unwanted interferon responses (Elbashir et al., 2001, *Nature*, 411:494-498). The antisense strand of the siRNA duplex serves as a sequence-specific guide that directs activity of an endoribonuclease function in the RNA induced silencing complex (RISC) to degrade target mRNA (Martinez et al., 2002, *Cell*, 110:563-574).

In studying the size limits for RNAi in *Drosophila* embryo extracts in vitro, a lower threshold of around 38 bp double-stranded RNA was established for activation of RNA interference using exogenously supplied double-stranded RNA and duplexes of 36, 30, and 29 bp length were without effect (Elbashir et al., 2001, *Genes & Dev.*, 15:188-200). The short 30-base RNAs were not cleaved into active 21-23-base siRNAs and therefore were deemed inactive for use in RNAi (Elbashir et al., 2001, *Genes & Dev.*, 15:188-200). Continuing to work in the *Drosophila* embryo extract system, the same group later carefully mapped the structural features needed for short chemically synthesized RNA duplexes to function as siRNAs in RNAi pathways. RNA duplexes of 21-bp length with 2-base 3'-overhangs were most effective, duplexes of 20, 22, and 23-bp length had slightly decreased potency but did result in RNAi mediated mRNA degradation, and 24 and 25-bp duplexes were inactive (Elbashir et al., 2001, *EMBO J.,* 20:6877-6888).

Some of the conclusions of these earlier studies may be specific to the *Drosophila* system employed. Other investigators established that longer siRNAs can work in human cells. However, duplexes in the 21-23-bp range have been shown to be more active and have become the accepted design (Caplen et al., 2001, *Proc. Natl. Acad. Sci. USA*, 98:9742-9747). Essentially, chemically synthesized duplex RNAs that mimicked the natural products that result from Dicer degradation of long duplex RNAs were identified to be the preferred compound for use in RNAi. Approaching this problem from the opposite direction, investigators studying size limits for RNAi in *C. elegans* found that although a microinjected 26-bp RNA duplex could function to suppress gene expression, it required a 250-fold increase in concentration compared with an 81-bp duplex (Parrish et al., 2000, *Mol. Cell,* 6:1077-1087).

Despite the attention given to RNAi research recently, the field is still in the early stages of development. Not all siRNA molecules are capable of targeting the destruction of their complementary RNAs in a cell. As a result, complex sets of rules have been developed for designing RNAi molecules that will be effective. Those having skill in the art expect to test multiple siRNA molecules to find functional compositions. (Ji et al. 2003) Some artisans pool several siRNA preparations together to increase the chance of obtaining silencing in a single study. (Ji et al. 2003) Such pools typically contain 20 nM of a mixture of siRNA oligonucleotide duplexes or more (Ji et al. 2003), despite the fact that a siRNA molecule can work at concentrations of 1 nM or less (Holen et al. 2002). This technique can lead to artifacts caused by interactions of the siRNA sequences with other cellular RNAs ("off target effects"). (Scherer et al. 2003) Off target effects can occur when the RNAi oligonucleotides have homology to unintended targets or when the RISC complex incorporates the unintended strand from and RNAi duplex. (Scherer et al. 2003) Generally, these effects tend to be more pronounced when higher concentrations of RNAi duplexes are used. (Scherer et al. 2003)

In addition, the duration of the effect of an effective RNAi treatment is limited to about 4 days (Holen et al. 2002). Thus, researchers must carry out siRNA experiments within 2-3 days of transfection with an siRNA duplex or work with plasmid or viral expression vectors to obtain longer term silencing.

Additional physical studies are needed to more completely characterize the structural requirements of RNAi active oligonucleotide duplexes to identify more potent and longer lasting compositions and/or methods that simplify site-selection difficulties. These studies should also include a detailed analysis of the interferon response. Ideally, such studies will be useful in identifying new RNAi active compounds that are more potent, that simplify the site selection process, and decrease "off target effects."

The invention provides RNAi compositions with increased potency, duration of action, and decreased "off target effects" that do not activate the interferon response and provides methods for their use. In addition, the compositions ease site selection criteria and provide a duration of action that is about twice as long as prior known compositions. These and other advantages of the invention, as well as additional inventive features, will be apparent from the description of the invention provided herein.

BRIEF SUMMARY OF THE INVENTION

The invention provides improved compositions and methods for selectively reducing the expression of a gene product from a desired target gene in a eukaryotic cell, as well as for treating diseases caused by the expression of the gene. The method involves introducing into the environment of a cell an amount of a double-stranded RNA (dsRNA) such that a sufficient portion of the dsRNA can enter the cytoplasm of the cell to cause a reduction in the expression of the target gene. The dsRNA has a first oligonucleotide sequence that is between 26 and about 30 nucleotides in length and a second oligonucleotide sequence that anneals to the first sequence under biological conditions, such as the conditions found in the cytoplasm of a cell. In addition, a region of one of the sequences of the dsRNA having a sequence length of from about 19 to about 23 nucleotides is complementary to a nucleotide sequence of the RNA produced from the target gene. A dsRNA composition of the invention is at least as active as any isolated 19, 20, 21, 22, or 23 basepair sequence that is contained within it. Pharmaceutical compositions containing the disclosed dsRNA compositions are also contemplated. The compositions and methods give a surprising increase in the potency and duration of action of the RNAi effect. Although the invention is not intended to be limited by the underlying theory on which it is believed to operate, it is thought that this increase in potency and duration of action are caused by the fact the dsRNA serves as a substrate for Dicer which appears to facilitate incorporation of one sequence from the dsRNA into the RISC complex that is directly responsible for destruction of the RNA from the target gene.

BRIEF DESCRIPTION OF THE DRAWINGS

In FIG. 1A, 50 nM of each dsRNA was used. In FIG. 1B, 1 nM of each dsRNA was used. In FIG. 1C, 200 pM of each dsRNA was used. In FIG. 1D, 50 pM of each dsRNA was used.

DETAILED DESCRIPTION OF THE INVENTION

Figure 1:
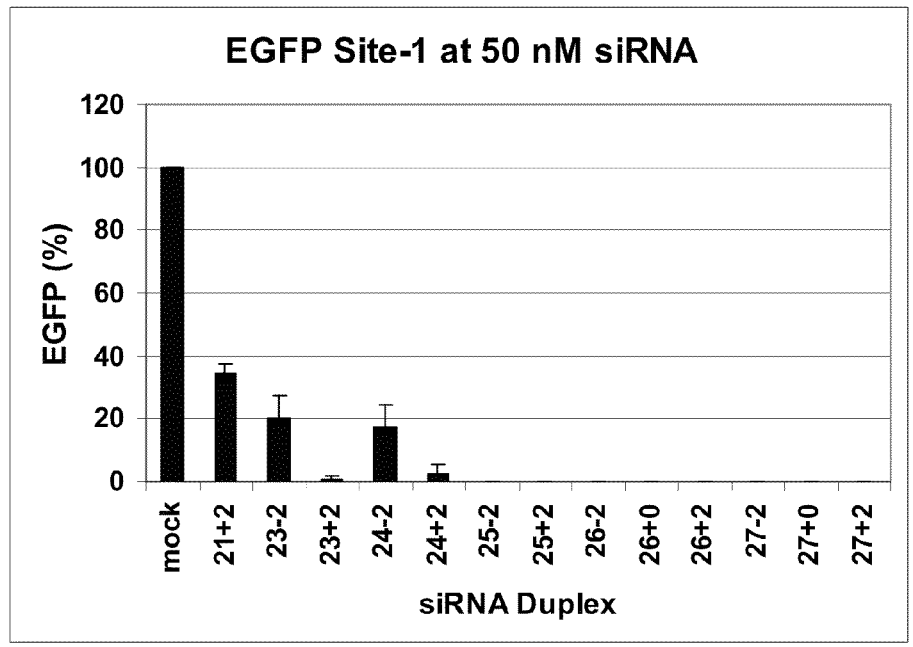
FIG. 1 provides a comparison of RNAi efficacy using several dsRNAs having variable length and formats including a two nucleotide 3' overhang (+2), a two nucleotide 5' overhang (−2), and blunt ends (+0). The sequences are disclosed in the Example 2. In each panel A-D 200 μg of reporter vector was co-transfected with the indicated concentration of dsRNA. Each bar represents the average of three duplicate experiments.
Figure 1:
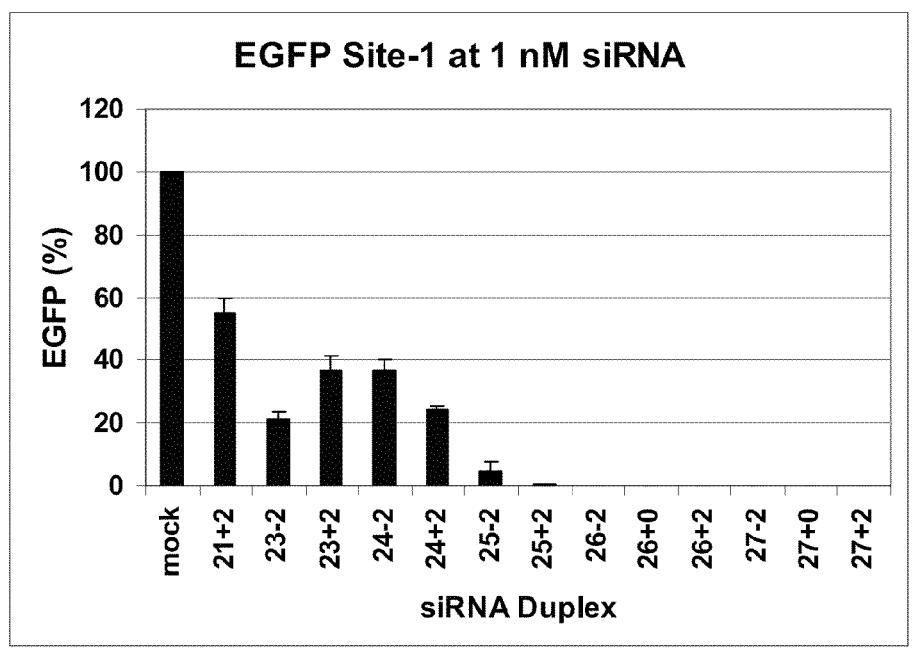
Figure 1:
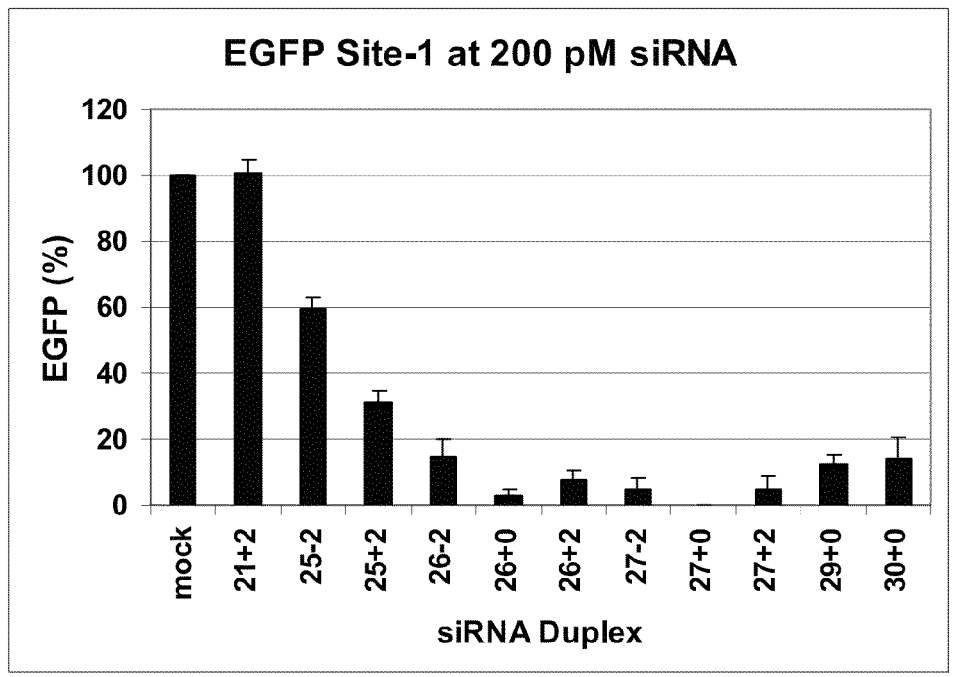
Figure 1:
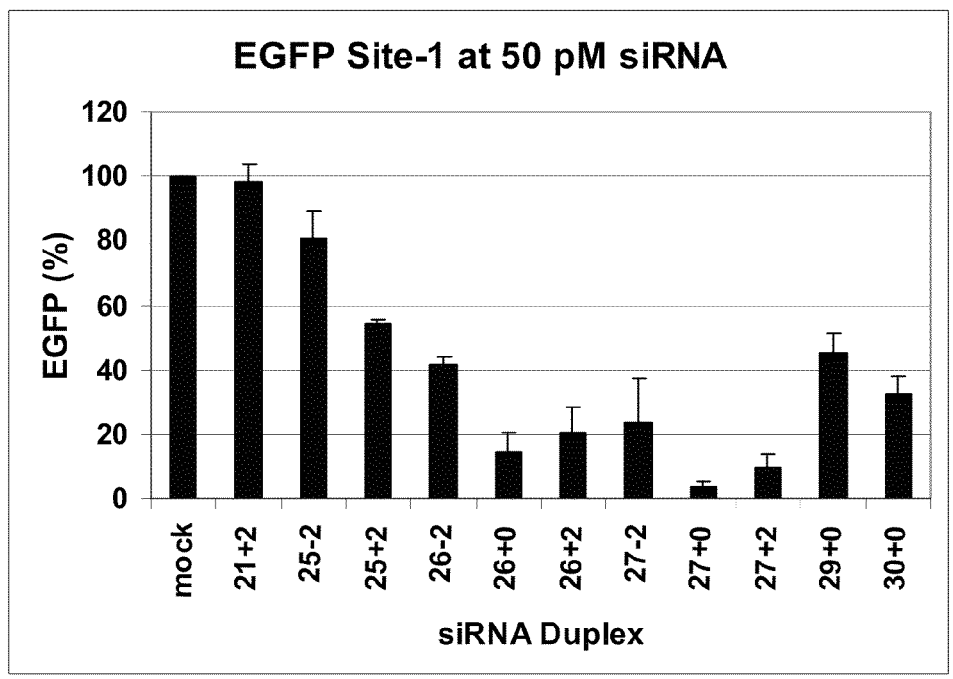

The invention is directed to compositions that contain double stranded RNA ("dsRNA"), and methods for preparing them, that are capable of reducing the expression of target genes in eukaryotic cells. One of the strands of the dsRNA contains a region of nucleotide sequence that has a length that ranges from about 19 to about 23 nucleotides that can direct the destruction of the RNA transcribed from the target gene.

For purposes of the invention a suitable dsRNA contains one oligonucleotide sequence, a first sequence, that is at least 25 nucleotides in length and no longer than about 30 nucleotides. More preferably this sequence of RNA is between about 26 and 29 nucleotides in length. Still more preferably this sequence is about 27 or 28 nucleotides in length, 27 nucleotides is most preferred. The second sequence of the dsRNA can be any sequence that anneals to the first sequence under biological conditions, such as within the cytoplasm of a eukaryotic cell. Generally, the second oligonucleotide sequence will have at least 19 complementary base pairs with the first oligonucleotide sequence, more typically the second oligonucleotides sequence will have about 21 or more complementary base pairs, and more preferably about 25 or more complementary base pairs with the first oligonucleotide sequence. In a preferred embodiment the second sequence is the same length as the first sequence.

In certain embodiments the double-stranded RNA structure the first and second oligonucleotide sequences exist on separate oligonucleotide strands which can be and typically are chemically synthesized. In preferred embodiments both strands are between 26 and 30 nucleotides in length. In one preferred embodiment both strands are 27 nucleotides in length, are completely complementary and have blunt ends. The dsRNA can be from a single RNA oligonucleotide that undergoes intramolecular annealing or, more typically, the first and second sequences exist on separate RNA oligonucleotides.

Suitable dsRNA compositions that contain two separate oligonucleotides can be chemically linked outside their annealing region by chemical linking groups. Many suitable chemical linking groups are known in the art and can be used. Suitable groups will not block Dicer activity on the dsRNA and will not interfere with the directed destruction of the RNA transcribed from the target gene.

The first and second oligonucleotide sequences are not required to be completely complimentary. In fact, it is preferred that the 3'-terminus of the sense strand contains one or more mismatches. It is more preferred that two mismatches be incorporated at the 3' terminus. In a most preferred embodiment the dsRNA of the invention is a double stranded RNA molecule containing two RNA oligonucleotides each of which is 27 nucleotides in length and, when annealed to each other, have blunt ends and a two nucleotide mismatch on the 3'-terminus of the sense strand (the 5'-terminus of the antisense strand).

One feature of the dsRNA compositions of the invention is that they can serve as a substrate for Dicer. Typically, the dsRNA compositions of this invention will not have been treated with Dicer, other RNAses, or extracts that contain them. Such treatments could digest the dsRNA to lengths of less than 25 nucleotides that are no longer Dicer substrates. Several methods are known and can be used for determining whether a dsRNA composition serves as a substrate for Dicer. For example, Dicer activity can be measured in vitro using the Recombinant Dicer Enzyme Kit (GTS, San Diego, Calif.) according to the manufacturer's instructions. Dicer activity can be measured in vivo by treating cells with dsRNA and maintaining them for 24 h before harvesting them and isolating their RNA. RNa can be isolated using standard methods, such as with the RNeasy™ Kit (Qiagen) according to the manufacturer's instructions. The isolated RNA can be separated on a 10% PAGE gel which is used to prepare a standard RNA blot that can be probed with a suitable labeled deoxyoligonucleotide, such as an oligonucleotide labeled with the Starfire™ Oligo Labeling System (Integrated DNA Technologies, Inc., Coralville, Iowa).

It has been found empirically that these longer dsRNA species of from 25 to about 30 nucleotides give unexpectedly improved results in terms of increased potency and increased duration of action over shorter prior art RNAi compositions. The dsRNA compositions of the invention are at least as active as any isolated 23 nucleotide dsRNA sequence contained within them and in preferred embodiments more active. Without wishing to be bound by the underlying theory of the invention, it is thought that the longer dsRNA species serve as a substrate for the enzyme Dicer in the cytoplasm of a cell. In addition to cleaving the dsRNA of the invention into shorter segments, Dicer is thought to facilitate the incorporation of a single-stranded cleavage product derived from the cleaved dsRNA into the RISC complex that is responsible for the destruction of the cytoplasmic RNA derived from the target gene. Studies have shown that the cleavability of a dsRNA species by Dicer corresponds with increased potency and duration of action of the dsRNA species.

Suitable dsRNA compositions of this invention do not induce apoptosis in the cells in which they are used. Apoptosis or "programmed cell death," includes any non-necrotic, cell-regulated form of cell death, as defined by criteria well established in the art. Cells undergoing apoptosis show characteristic morphological and biochemical features. Once the process is triggered, or the cells are committed to undergoing apoptosis, morphological and physiological changes include cell shrinkage, chromatin condensation, nuclear and cytoplasmic condensation, membrane blebbing, partitioning of cytoplasm and nucleus into membrane bound vesicles which contain ribosomes (apoptotic bodies), and DNA degradation into a characteristic oligonucleosomal ladder composed of multiples of 200 base pairs, leading eventually to cell death. In vivo, these apoptotic bodies are rapidly recognized and phagocytized by either macrophages or adjacent epithelial cells. In vitro, the apoptotic bodies as well as the remaining cell fragments ultimately swell and finally lyse. This terminal phase of in vitro cell death has been termed "secondary necrosis."

The effect that a dsRNA has on a cell can depend upon the cell itself. In some circumstances a dsRNA could induce apoptosis or gene silencing in one cell type and not another. Thus, it is possible that a dsRNA could be suitable for use in one cell and not another. To be considered "suitable" a dsRNA composition need not be suitable under all possible circumstances in which it might be used, rather it need only be suitable under a particular set of circumstances.

Modifications can be included in the disclosed dsRNA so long as the dsRNA remains sufficiently chemically stable, does not induce apoptosis, does not substantially interrupt annealing of the first and second strands, and otherwise does not substantially interfere with the directed destruction of the RNA transcribed from the target gene. Modifications can be incorporated in the 3'-terminal region, the 5'-terminal region, in both the 3'-terminal and 5'-terminal region or in some instances throughout the sequence. With the restrictions noted above in mind any number and combination of modifications can be incorporated into the dsRNA. Where multiple modifications are present, they may be the same or different.

Modifications to bases, sugar moieties, the phosphate backbone, and their combinations are contemplated.

For example, either the 3' or 5' terminal regions of the sequences in a dsRNA can be phosphorylated or biotinylated. Examples of modifications contemplated for the phosphate backbone include phosphonates, including methylphosphonate, phosphorothioate, and phosphotriester modifications such as alkylphosphotriesters, and the like. Examples of modifications contemplated for the sugar moiety include 2'-alkyl pyrimidine, such as 2'-O-methyl, 2'-fluoro, amino, and deoxy modifications and the like. Examples of modifications contemplated for the base groups include abasic sugars, 2-O-alkyl modified pyrimidines, 4-thiouracil, 5-bromouracil, 5-iodouracil, and 5-(3-aminoallyl)-uracil and the like. Many other modifications are known and can be used so long as the above criteria are satisfied The double-stranded RNA sample can be suitably formulated and introduced into the environment of the cell by any means that allows for a sufficient portion of the sample to enter the cell to induce gene silencing, if it is to occur. Many formulations for dsRNA are known in the art and can be used so long as dsRNA gains entry to the target cells so that it can act. For example, dsRNA can be formulated in buffer solutions such as phosphate buffered saline solutions, liposomes, micellar structures, and capsids. Formulations of dsRNA with cationic lipids can be used to facilitate transfection of the dsRNA into cells. Suitable lipids include Oligofectamine, Lipofectamine (Life Technologies), NC388 (Ribozyme Pharmaceuticals, Inc., Boulder, Colo.), or FuGene 6 (Roche) all of which can be used according to the manufacturer's instructions.

It can be appreciated that the method of introducing dsRNA into the environment of the cell will depend on the type of cell and the make up of its environment. For example, when the cells are found within a liquid, one preferable formulation is with a lipid formulation such as in lipofectamine and the dsRNA can be added directly to the liquid environment of the cells. Lipid formulations can also be administered to animals such as by intravenous, intramuscular, or intraperitoneal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate dsRNA in a buffer or saline solution and directly inject the formulated dsRNA into cells, as in studies with oocytes. The direct injection of dsRNA duplexes Suitable amounts of dsRNA must be introduced and these amounts can be empirically determined using standard methods. Typically, effective concentrations of individual dsRNA species in the environment of a cell will be about 50 nanomolar or less 10 nanomolar or less, more preferred are compositions in which concentrations of about 1 nanomolar or less can be used. Even more preferred are methods that utilize a concentration of about 200 picomolar or less and even a concentration of about 50 picomolar or less can be used in many circumstances.

The method can be carried out by addition of the dsRNA compositions to any extracellular matrix in which cells can live provided that the dsRNA composition is formulated so that a sufficient amount of the dsRNA can enter the cell to exert its effect. For example, the method is amenable for use with cells present in a liquid such as a liquid culture or cell growth media, in tissue explants, or in whole organisms, including animals, such as mammals and especially humans.

As is known, RNAi methods are applicable to a wide variety of genes in a wide variety of organisms and the disclosed compositions and methods can be utilized in each of these contexts. Examples of genes which can be targeted by the disclosed compositions and methods include endogenous genes which are genes that are native to the cell or to genes that are not normally native to the cell. Without limitation these genes include oncogenes, cytokine genes, idiotype (Id) protein genes, prion genes, genes that expresses molecules that induce angiogenesis, genes for adhesion molecules, cell surface receptors, proteins involved in metastasis, proteases, apoptosis genes, cell cycle control genes, genes that express EGF and the EGF receptor, multi-drug resistance genes, such as the MDR1 gene.

Expression of a target gene can be determined by any suitable method now known in the art or that is later developed. It can be appreciated that the method used to measure the expression of a target gene will depend upon the nature of the target gene. For example, when the target gene encodes a protein the term "expression" can refer to a protein or transcript derived from the gene. In such instances the expression of a target gene can be determined by measuring the amount of mRNA corresponding to the target gene or by measuring the amount of that protein. Protein can be measured in protein assays such as by staining or immunoblotting or, if the protein catalyzes a reaction that can be measured, by measuring reaction rates. All such methods are known in the art and can be used. Where the gene product is an RNA species expression can be measured by determining the amount of RNA corresponding to the gene product. Several specific methods for detecting gene expression are described in Example 1. The measurements can be made on cells, cell extracts, tissues, tissue extracts or any other suitable source material.

The determination of whether the expression of a target gene has been reduced can be by any suitable method that can reliably detect changes in gene expression. Typically, the determination is made by introducing into the environment of a cell undigested dsRNA such that at least a portion of that dsRNA enters the cytoplasm and then measuring the expression of the target gene. The same measurement is made on identical untreated cells and the results obtained from each measurement are compared. When the method appears to reduce the expression of the target gene by about 10% or more (which is equivalent to about 90% or less) of the level in an untreated organism, for purposes of this invention, the method is considered to reduce the expression of the target gene. Typically, the method can be used to reduce the expression of a target gene by far more than 10%. In some instances the method can be used to reduce the expression by about 50% or more, in more preferred methods the expression is reduced by about 75% or more, still more preferable are methods that reduce the expression by about 90% or more, or even about 95% or more, or about 99% or more or even by completely eliminating expression of the target gene.

The dsRNA can be formulated as a pharmaceutical composition which comprises a pharmacologically effective amount of a dsRNA and pharmaceutically acceptable carrier. A pharmacologically or therapeutically effective amount refers to that amount of a dsRNA effective to produce the intended pharmacological, therapeutic or preventive result. The phrases "pharmacologically effective amount" and "therapeutically effective amount" or simply "effective amount" refer to that amount of an RNA effective to produce the intended pharmacological, therapeutic or preventive result. For example, if a given clinical treatment is considered effective when there is at least a 20% reduction in a measurable parameter associated with a disease or disorder, a therapeutically effective amount of a drug for the treatment of that disease or disorder is the amount necessary to effect at least a 20% reduction in that parameter.

The phrase pharmaceutically acceptable carrier refers to a carrier for the administration of a therapeutic agent. Exemplary carriers include saline, buffered saline, dextrose, water, glycerol, ethanol, and combinations thereof. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. The pharmaceutically acceptable carrier of the disclosed dsRNA composition may be micellar structures, such as a liposomes, capsids, capsoids, polymeric nanocapsules, or polymeric microcapsules.

Polymeric nanocapsules or microcapsules facilitate transport and release of the encapsulated or bound dsRNA into the cell. They include polymeric and monomeric materials, especially including polybutylcyanoacrylate. A summary of materials and fabrication methods has been published (see J. Kreuter, (1991) Nanoparticles-preparation and applications. In: M. Donbrow (Ed.) Microcapsules and nanoparticles in medicine and pharmacy. CRC Press, Boca Raton, Fla., pp. 125-14). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Suitably formulated pharmaceutical compositions of this invention can be administered by any means known in the art such as by parenteral routes, including intravenous, intramuscular, intraperitoneal, subcutaneous, transdermal, airway (aerosol), rectal, vaginal and topical (including buccal and sublingual) administration.

In general a suitable dosage unit of dsRNA will be in the range of 0.001 to 0.25 milligrams per kilogram body weight of the recipient per day, preferably in the range of 0.01 to 20 micrograms per kilogram body weight per day, more preferably in the range of 0.01 to 10 micrograms per kilogram body weight per day, even more preferably in the range of 0.10 to 5 micrograms per kilogram body weight per day, and most preferably in the range of 0.1 to 2.5 micrograms per kilogram body weight per day. Preferably, pharmaceutical composition comprising the dsRNA is administered once daily. However, the therapeutic agent may also be dosed in dosage units containing two, three, four, five, six or more sub-doses administered at appropriate intervals throughout the day. In that case, the dsRNA contained in each sub-dose must be correspondingly smaller in order to achieve the total daily dosage unit. The dosage unit can also be compounded for a single dose over several days, e.g., using a conventional sustained release formulation which provides sustained and consistent release of the dsRNA over a several day period. Sustained release formulations are well known in the art. In this embodiment, the dosage unit contains a corresponding multiple of the daily dose. Regardless of the formulation, the pharmaceutical composition must contain dsRNA in a quantity sufficient to inhibit expression of the target gene in the animal or human being treated. The composition can be compounded in such a way that the sum of the multiple units of dsRNA together contain a sufficient dose.

Data can be obtained from cell culture assays and animal studies to formulate a suitable dosage range for humans. The dosage of compositions of the invention lies, preferably, within a range of circulating concentrations that include the ED50 (as determined by known methods) with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range of the compound that includes the IC50 (i.e., the concentration of the test compound which achieves a half-maximal inhibition of symptoms) as determined in cell culture. Such information can be used to more accurately determine useful doses in humans. Levels of dsRNA in plasma may be measured by standard methods, for example, by high performance liquid chromatography.

The following examples further illustrate the invention but, of course, should not be construed as in any way limiting its scope.

EXAMPLE 1

This example demonstrates the preparation of double-stranded RNA oligonucleotides Oligonucleotide Synthesis and Purification.

RNA oligonucleotides were synthesized using solid phase phosphoramidite chemistry, deprotected and desalted on NAP-5 columns (Amersham Pharmacia Biotech, Piscataway, N.J.) using standard techniques (Damha and Olgivie, *Methods Mol Biol* 1993, 20:81-114; Wincott et al., *Nucleic Acids Res* 1995, 23:2677-84). The oligomers were purified using ion-exchange high performance liquid chromatography (IE-HPLC) on an Amersham Source 15Q column (1.0 cm×25 cm) (Amersham Pharmacia Biotech, Piscataway, N.J.) using a 15 min step-linear gradient. The gradient varied from 90:10 Buffers A:B to 52:48 Buffers A:B, where Buffer A was 100 mM Tris pH 8.5 and Buffer B was 100 mM Tris pH 8.5, 1 M NaCl. Samples were monitored at 260 nm and peaks corresponding to the full-length oligonucleotide species were collected, pooled, desalted on NAP-5 columns, and lyophilized.

The purity of each oligomer was determined by capillary electrophoresis (CE) on a Beckman PACE 5000 (Beckman Coulter, Inc., Fullerton, Calif.). The CE capillaries had a 100 nm inner diameter and contained ssDNA 100R Gel (Beckman-Coulter). Typically, about 0.6 nmole of oligonucleotide was injected into a capillary, ran in an electric field of 444 V/cm and detected by UV absorbance at 260 nm. Denaturing Tris-Borate-7 M-urea running buffer was purchased from Beckman-Coulter. Oligoribonucleotides were at least 90% pure as assessed by CE for use in experiments described below. Compound identity was verified by matrix-assisted laser desorption ionization time-of-flight (MALDI-TOF) mass spectroscopy on a Voyager DE™ Biospectometry Work Station (Applied Biosystems, Foster City, Calif.) following the manufacturer's recommended protocol. Relative molecular masses of all oligomers were within 0.2% of expected molecular mass.

Preparation of Duplexes.

Single-stranded RNA (ssRNA) oligomers were resuspended at 100 μM concentration in duplex buffer consisting of 100 mM potassium acetate, 30 mM HEPES, pH 7.5.

Complementary sense and antisense strands were mixed in equal molar amounts to yield a final solution of 50 μM duplex. Samples were heated to 95° C. for 5' and allowed to cool to room temperature before use. Double-stranded RNA (dsRNA) oligomers were stored at −20° C. Single-stranded RNA oligomers were stored lyophilized or in nuclease-free water at −80° C.

Nomenclature.

For consistency, the following nomenclature has been employed throughout the Examples. Names given to duplexes indicate the length of the oligomers and the presence or absence of overhangs. A "21+2" duplex contains two RNA strands both of which are 21 nucleotides in length, also termed a 21-mer siRNA duplex, and having a 2 base 3'-overhang. A "21-2" design is a 21-mer siRNA duplex with a 2 base 5'-overhang. A 21-0 design is a 21-mer siRNA duplex with no overhangs (blunt). A "21+2UU" is a 21-mer duplex with 2-base 3'-overhang and the terminal 2 bases at the 3'-ends are both U residues (which may result in mismatch with target sequence).

EXAMPLE 2

This example demonstrates that dsRNAs having strands that are 25 nucleotides in length or longer have surprisingly increased potency in mammalian systems than known 21-23-mer siRNAs.

Cell Culture, Transfection, and EGFP Assays.

Human embryonic kidney (HEK) 293 cells were grown in DMEM medium supplemented with 10% fetal bovine serum (FBS) (Irvine Scientific, Santa Ana, Calif.). Transfections were done at 90% confluence in 24-well plates using Lipofectamine 2000 (Invitrogen, Carlsbad, Calif.) according to the manufacturer's instructions. Briefly, 50 µl of Opti-MEM media was mixed with nucleic acids, including siRNA duplexes and/or 100-200 ng plasmid pEGFP-C1 (Clontech, Palo Alto, Calif.) for 5 min. Nucleic acids were then mixed with 50 µl of Opti-MEM media that had been pre-mixed with 1.5 µl of Lipofectamine 2000 and incubated at room temperature for 15 min. The lipid-nucleic acid mixtures were added to cells after removal of old media and swirled and then an additional 0.4 ml of media pre-warmed to 37° C. was added. Incubation was continued at 37° C. and cells were assayed for fluorescence at the times indicated. Each assay was performed in triplicate. EGFP expression levels were measured by direct fluorescence in a fluorescence-activated cell sorter (FACS) (Moslo-MLS, Dako Cytomation, Fort Collins, Colo.) in the City of Hope Cytometrics Core Facility (Duarte, Calif.). EGFP expression was measured as the percentage of cells showing detectable fluorescence above background (mock-transfected negative control cells).

NIH 3T3 cells that stably expressed EGFP (Kim and Rossi, 2003, *Antisense Nucleic Acid Drug Dev.*, 13:151-155) were grown in DMEM media supplemented with 10% FBS. Cells were plated at 30% density on 24-well plates and transfected with siRNA alone without reporter plasmid using the same method described above. Media was changed at 24 h and EGFP assays were performed at 3, 6 and 9 days post-transfection. At 3 days post-transfection, $1 \times 10^5$ cells were used for extract preparation and $1 \times 10^4$ cells were re-plated and continued incubation for later assay. At day 6, $1 \times 10^5$ cells were used for extract preparation, and $1 \times 10^4$ cells were re-plated and continued incubation for later assay. At day 9, $1 \times 10^5$ cells were used for extract preparation. For extract preparation, $1 \times 10^5$ cells were suspended in 300 µl phosphate buffered saline (PBS) and sonicated for 10 sec. Cells were centrifuged at 14,000 g for 2 min and cell supernatant was recovered for fluorometry. EGFP fluorescence was examined using a VersaFluor Cuvette Fluorometer (Bio-Rad, Hercules, Calif.) using excitation filter D490 and emission filter D520. Percentage of EGFP expression was determined relative to extract prepared from non-transfected control cells.

In addition, cells were directly examined by fluorescence microscopy using a Nikon Eclipse TE2000-S (Nikon Instech Co., Kanagawa, JP) using the program Spot v3.5.8. Images were digitally captured with identical exposure times so that comparisons between cells samples could be made.

Nucleic Acid Reagents.

The reporter system employed EGFP either as a transfection plasmid vector pEGFP-C1 (Clontech, Palo Alto, Calif.) or as a stable transformant in an NIH 3T3 cell line. The coding sequence of EGFP is shown below, from Genbank accession #U55763. The ATG start codon and TAA stop codons are highlighted in bold font and sites target by siRNA reagents are underscored.

```
SEQ ID NO. 1:
atggtgagcaagggcgaggagctgttcaccggggtggtgcccatcctggtcgagctggacggcgacgtaaacggcca caagttcagcgtgtccggcgagggcgagggcgatgccacctacggcaagctgaccctgaagttcatctgcaccaccg gcaagctgcccgtgccctggcccaccctcgtgaccaccctgacctacggcgtgcagtgcttcagccgctaccccgac cacatgaagcagcacgacttctttcaagtccgccatgcccgaaggctacgtccaggagcgcaccatcttcttcaagga cgacggcaactacaagacccgcgccgaggtgaagttcgagggcgacaccctggtgaaccgcatcgagctgaagggca tcgacttcaaggaggacggcaacatcctgggcacaagctggagtacaactacaacagccacaacgtctatatcatg gccgacaagcagaagaacggcatcaaggtgaacttcaagatccgccacaacatcgaggacggcagcgtgcagctcgc cgaccactaccagcagaacacccccatcggcgacggccccgtgctgctgcccgacaaccactacctgagcacccagt ccgccctgagcaaagacccaacgagaagcgcgatcacatggtcctgctggagttcgtgaccgccgcgggatcact ctcggcatggacgagctgtacaagtaa
```

Site-1 used for siRNA targeting in EGFP was:

SITE 1:
(SEQ ID NO: 67)
5' GCAAGCUGACCCUGAAGUUCAUCUGCACCACCGGCAAGC 3'

Site-2 used for siRNA targeting in EGFP was:

SITE 2:
(SEQ ID NO: 68)
5' UGAAGCAGCACGACUUCUUCAAGUCCGCCAUG 3'

RNA duplexes were synthesized and prepared as described in Example 1. RNA duplexes targeting EGFP Site-1 are summarized in Table 1 below. Some sequences had the dinucleotide sequence "UU" placed at the 3'-end of the sense strand (Elbashir et al., 2001, *EMBO J.*, 20:6877-6888; Hohjoh, 2002, *FEBS Lett.*, 521:195-199). Mismatches that resulted from including 3'-terminal "UU" or where a mismatch was intentionally positioned are highlighted in bold and underscored.

TABLE 1

Summary of Oligonucleotide Reagents, EGFP Site-1

| Sequence | Name | SEQ ID NOo. |
|---|---|---|
| 5' GCAAGCUGACCCUGAAGUUCAUCUGCACCACCGGCAAGC 3' | EGFP Site-1 | SEQ ID NO: 67 |
| 5' GCAAGCUGACCCUGAAGUUCA<br>3' UUCGACUGGGACUUCAAGUAG | EGFPS1-21 − 2 | SEQ ID No. 2<br>SEQ ID NO. 3 |
| 5' AAGCUGACCCUGAAGUUCAUC<br>3' UUCGACUGGGACUUCAAGUAG | EGFPS1-21 + 0 | SEQ ID No. 4<br>SEQ ID NO. 5 |
| 5' GCUGACCCUGAAGUUCAUCUG<br>3' UUCGACUGGGACUUCAAGUAG | EGFPS1-21 + 2(7) | SEQ ID No. 6<br>SEQ ID NO. 7 |
| 5' GCAAGCUGACCCUGAAGUUCAUU<br>3' UUCGACUGGGACUUCAAGUAGAC | EGFPS1-23 − 2UU | SEQ ID No. 8<br>SEQ ID NO. 9 |
| 5' GCUGACCCUGAAGUUCAUCUGUU<br>3' UUCGACUGGGACUUCAAGUAGAC | EGFPS1-23 + 2UU | SEQ ID No. 10<br>SEQ ID NO. 11 |
| 5' GCAAGCUGACCCUGAAGUUCAUUU<br>3' UUCGACUGGGACUUCAAGUAGACG | EGFPS1-24 − 2UU | SEQ ID No. 12<br>SEQ ID NO. 13 |
| 5' GCUGACCCUGAAGUUCAUCUGCUU<br>3' UUCGACUGGGACUUCAAGUAGACG | EGFPS1-24 + 2UU | SEQ ID No. 14<br>SEQ ID NO. 15 |
| 5' GCAAGCUGACCCUGAAGUUCAUCUU<br>3' UUCGACUGGGACUUCAAGUAGACGU | EGFPS1-25 − 2UU | SEQ ID No. 16<br>SEQ ID NO. 17 |
| 5' GCUGACCCUGAAGUUCAUCUGCAUU<br>3' UUCGACUGGGACUUCAAGUAGACGU | EGFPS1-25 + 2UU | SEQ ID No. 18<br>SEQ ID NO. 19 |
| 5' AAGCUGACCCUGAAGUUCAUCUGCAC<br>3' UUCGACUGGGACUUCAAGUAGACGUG | EGFPS1-26 + 0 | SEQ ID No. 20<br>SEQ ID NO. 21 |
| 5' AAGCUGACCCUGAAGUUCAUCUGCUU<br>3' UUCGACUGGGACUUCAAGUAGACGUG | EGFPS1-26 + 0UU | SEQ ID No. 22<br>SEQ ID NO. 23 |
| 5' GCAAGCUGACCCUGAAGUUCAUCUUU<br>3' UUCGACUGGGACUUCAAGUAGACGUG | EGFPS1-26 − 2UU | SEQ ID No. 24<br>SEQ ID NO. 25 |
| 5' GCUGACCCUGAAGUUCAUCUGCACUU<br>3' UUCGACUGGGACUUCAAGUAGACGUG | EGFPS1-26 + 2UU | SEQ ID No. 26<br>SEQ ID NO. 27 |
| 5' AAGCUGACCCUGAAGUUCAUCUGCACC<br>3' UUCGACUGGGACUUCAAGUAGACGUGG | EGFPS1-27 + 0 | SEQ ID No. 28<br>SEQ ID NO. 29 |
| 5' AAGCUGACCCUGAAGUUCAUCUGCAUU<br>3' UUCGACUGGGACUUCAAGUAGACGUGG | EGFPS1-27 + 0UU | SEQ ID No. 30<br>SEQ ID NO. 31 |
| 5' GCAAGCUGACCCUGAAGUUCAUCUGUU<br>3' UUCGACUGGGACUUCAAGUAGACGUGG | EGFPS1-27 − 2UU | SEQ ID No. 32<br>SEQ ID NO. 33 |
| 5' GCUGACCCUGAAGUUCAUCUGCACAUU<br>3' UUCGACUGGGACUUCAAGUAGACGUGG | EGFPS1-27 + 2UU, mut | SEQ ID No. 34<br>SEQ ID NO. 35 |
| 5' AACCUGACCCUGUUCAUCAUCUCCACC<br>3' UUCGACUGGGACAAGUAGUAGACCUGG | EGFPS1-27 + 0-mut | SEQ ID No. 36<br>SEQ ID NO. 37 |
| 5' AAGCUGACCCUGAAGUUCAUCUGCACCA<br>3' UUCGACUGGGACUUCAAGUAGACGUGGU | EGFPS1-28 + 0 | SEQ ID No. 38<br>SEQ ID NO. 39 |
| 5' AAGCUGACCCUGAAGUUCAUCUGCACCAC<br>3' UUCGACUGGGACUUCAAGUAGACGUGGUG | EGFPS1-29 + 0 | SEQ ID No. 40<br>SEQ ID NO. 41 |
| 5' AAGCUGACCCUGAAGUUCAUCUGCACCACC<br>3' UUCGACUGGGACUUCAAGUAGACGUGGUGG | EGFPS1-30 + 0 | SEQ ID No. 42<br>SEQ ID NO. 43 |

Results.

HEK 293 cells were mock transfected (negative control), transfected with 200 ng EGFP reporter plasmid alone (positive control), or reporter plasmid+siRNA duplexes at varying concentrations. EGFP expression was assessed using the FACS assay at 24 h post-transfection. Results are shown in FIG. 1. At 50 nM concentration (FIG. 1A), a 21-mer siRNA duplex with 2-base 3'-overhang (21+2 design) (SEQ ID NoS. 6/7) showed about a 70% reduction in EGFP expression while longer duplexes were more potent. 25-mer siRNA duplexes (SEQ ID Nos. 16/17 and 18/19) and longer (SEQ ID Nos. 20/21, 24/25, 26/27, 30/31, 32/33, and 34/35) suppressed EGFP below detection limits. Typically, 21-mer siRNA oligos are employed at 10-100 nM concentration by those skilled in the art. At 1 nM concentration (FIG. 1B), a concentration much lower than is typically employed today, the 21-mer duplex showed only about a 40% reduction in EGFP expression while longer duplexes continued to suppress EGFP below detection limits. At 200 pM concentration (FIG. 1C), the 21-mer duplex had no effect on EGFP expression while the blunt 27-mer duplex continued to suppress EGFP below detection limits. At 50 pM concentration (FIG. 1D), the 27-mer blunt duplex (SEQ ID No. 30/31) suppressed EGFP expression by about 90% or more. The longer and shorter duplexes tested (26-mers SEQ ID No. 22/23, 24/25, 26/27; 29-mer SEQ ID No. 40/41; or 30-mer SEQ ID No. 42/43) were slightly less effective than the blunt 27-mer.

Figure 2:
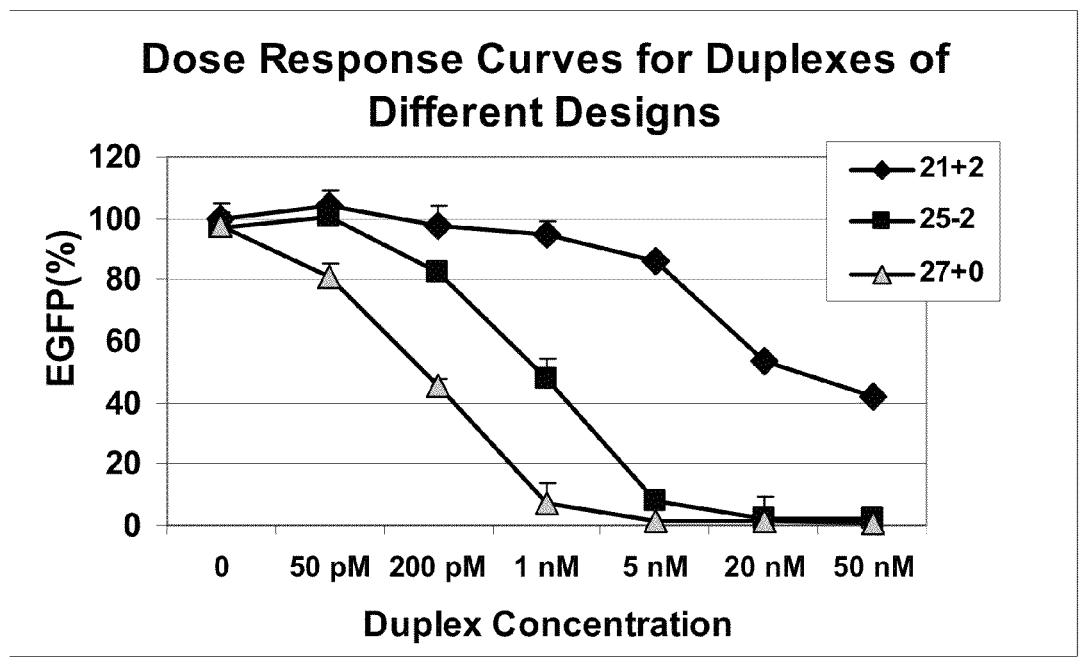
FIG. 2 shows an RNAi assay in 3T3 cells expressing endogenous EGFP. The experimental procedure is described in Example 2. Measurements were made 4 days after treatment. The dose response curves for 21-mer duplex with 2-base 3'-overhang (SEQ ID No. 6/7), 25-mer duplex with 2-base 5'-overhang (SEQ ID Nos. 16/17), and blunt 27-mer duplex (SEQ ID Nos. 30/31) are shown.

This experiment was repeated using NIH 3T3 cells that stably express EGFP. EGFP protein was detected in cellular extracts using a cuvette fluorometer as described above. The dose response curves for 21-mer duplex with 2-base 3'-overhang (SEQ ID No. 6/7), 25-mer duplex with 2-base 5'-overhang (SEQ ID Nos. 16/17), and blunt 27-mer duplex (SEQ ID Nos. 30/31) are shown in FIG. 2. The exact level of suppression varied between experiments done using stably transfected 3T3 cells compared with transiently transfected HEK 293 cells (FIG. 1), however qualitative trends were identical.

This example demonstrates that the longer dsRNAs of the invention have about a 100-fold or more higher potency than traditional 21-mer siRNAs. The enhanced effect was first seen at about a 25-mer length and maximal potency was achieved with a 27-mer. Potent RNAi effects were observed for 30-mer duplexes (the longest compounds tested herein), with no apparent toxicity to either the HEK 293 cells or NIH 3T3 cells. Furthermore, as duplex length was increased above 25-mer length (presumably when the duplex is sufficiently long to be a Dicer substrate), a 2-base 3'-overhang (as taught in the prior art) is no longer necessary. In the present experiments 25-mer duplexes with a 2-base 5'-overhang had similar potency as did blunt ended duplexes or duplexes with a 2-base 3'-overhang. In the current experimental system, the 27-mer blunt duplex showed greatest potency.

Figure 3:
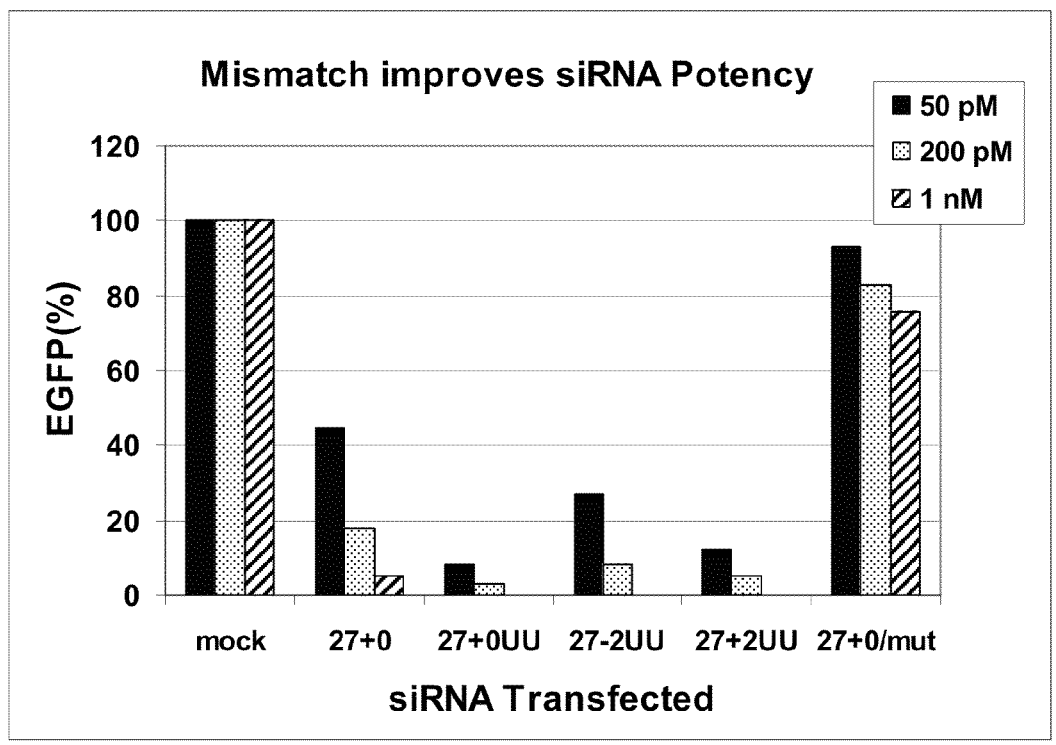
FIG. 3 shows RNAi assays of various 27-mer RNA duplex formats as outlined in Example 2. Duplex 27+0UU (SEQ ID Nos. 30/31) was most potent.

Within the set of 27-mer RNA duplexes tested in this example, duplexes that included base mismatches between the sense and antisense strands (SEQ ID Nos. 30/31, 32/33, 34/35) were more potent than the duplex having perfect complementarity (SEQ ID Nos. 28/29). These duplexes (27+ 0UU, 27+2UU, and 27-2UU) had 1 or 2 mismatches at the 3'-end of the sense strand. The set of 27-mer duplexes were compared for effective suppression of EGFP expression in the HEK 293 cell transient transfection assay and the results are shown in FIG. 3. Duplex 27+0UU (SEQ ID Nos. 30/31) was most potent The use of mismatches or decreased thermodynamic stability (specifically at the 3'-sense/5'-antisense position) has been proposed to facilitate or favor entry of the antisense strand into RISC (Schwarz et al., 2003, *Cell*, 115:199-208; Khvorova et al., 2003, *Cell*, 115:209-216), presumably by affecting some rate-limiting unwinding steps that occur with entry of the siRNA into RISC. Because of this terminal base composition has been included in design algorithms for selecting active 21-mer siRNA duplexes (Ui-Tei et al., 2004, *Nucleic Acids Res.*, 32:936-948; Reynolds et al., 2004, *Nat. Biotechnol.*, 22:326-330). It has been proposed that the 27-mer duplexes employed in this example do not directly enter RISC but first are cleaved by Dicer into 21-mer siRNAs. With Dicer cleavage, the small end-terminal sequence which contains the mismatches will either be left unpaired with the antisense strand (become part of a 3'-overhang) or be cleaved entirely off the final 21-mer siRNA. These "mismatches", therefore, do not persist as mismatches in the final RNA component of RISC. It was surprising to find that base mismatches or destabilization of segments at the 3'-end of the sense strand of a Dicer substrate improve the potency of synthetic duplexes in RNAi, presumably by facilitating processing by Dicer.

EXAMPLE 3

This example demonstrates that the use of 25-30 nucleotide RNA duplexes allows gene targeting at a site that could not be effectively targeted using traditional siRNA 21-mer designs.

It is currently expected in the art that the majority of 21-mer siRNA duplexes targeted to sites within a given target gene sequence will be ineffective (Holen et al., 2002, *Nucleic Acids Res.*, 30:1757-1766). Consequently, a variety of sites are commonly tested in parallel or pools containing several distinct siRNA duplexes specific to the same target with the hope that one of the reagents will be effective (Ji et al., 2003, *FEBS Lett.*, 552:247-252). To overcome the need to pool or engage in large scale empiric testing, complex design rules and algorithms have been devised to increase the likelihood of obtaining active RNAi effector molecules (Schwarz et al., 2003, *Cell*, 115:199-208; Khvorova et al., 2003, *Cell*, 115:209-216; Ui-Tei et al., 2004, *Nucleic Acids Res.*, 32:936-948; Reynolds et al., 2004, *Nat. Biotechnol.*, 22:326-330). These design rules significantly limit the number of sites amenable to RNAi knockdown within a given target gene. In fact, the design can be overly restrictive in situations demanding the suppression of specific alleles or isoforms. Moreover, the rules are not perfect and do not always provide active siRNA effector molecules. This example shows that the use of dsRNA duplexes of the present invention allow RNAi targeting at sites that were ineffectively targeted by previously known 21-mer siRNA reagents. This result minimizes the need for empirically testing multiple sites or using pooled reagent sets.

Nucleic Acid Reagents.

The reporter system employed EGFP as in SEQ ID No. 1 above. Site-2 in EGFP, as shown in Example 1, was targeted. RNA duplexes were synthesized and prepared as described in Example 1. RNA duplexes targeting EGFP Site-2 are summarized in Table 2 below. Duplex EGFPS2-27+0 mm was a blunt 27-mer duplex with a 2 base mismatch at the terminal 2 bases of the sense strand. These bases are shown in bold and underscored.

TABLE 2

Summary of Oligonucleotide Reagents, EGFP Site-2

| Sequence | Name | SEQ ID No. |
|---|---|---|
| 5' UGAAGCAGCACGACUUCUUCAAGUCCGCCAUG 3' | EGFP Site-2 | SEQ ID NO: 68 |
| 5' GCAGCACGACUUCUUCAAGUU<br>3' UUCGUCGUGCUGAAGAAGUUC | EGFPS2-21 + 2 | SEQ ID No. 44<br>SEQ ID No. 45 |
| 5' AAGCAGCACGACUUCUUCAAGUCCGCC<br>3' UUCGUCGUGCUGAAGAAGUUCAGGCGG | EGFPS2-27 + 0 | SEQ ID No. 46<br>SEQ ID No. 47 |
| 5' AAGCAGCACGACUUCUUCAAGUCC<u>GG</u><br>3' UUCGUCGUGCUGAAGAAGUUCAGGCGG | EGFPS2-27 + 0 mm | SEQ ID No. 48<br>SEQ ID No. 49 |

Results.

Figure 4:
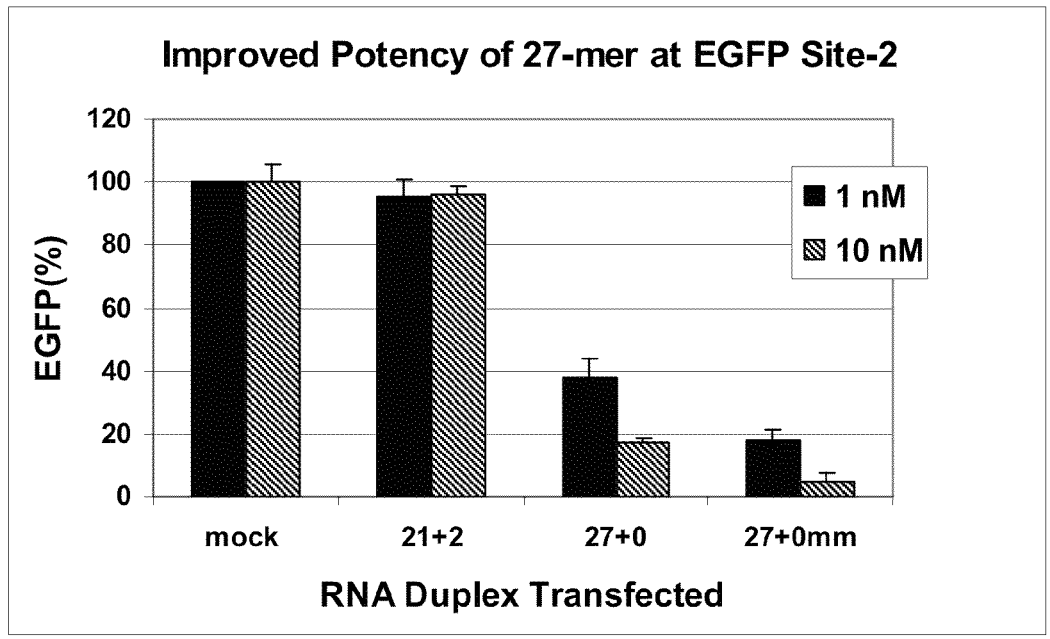
FIG. 4 shows RNAi assays on HEK 293 cells that were either mock transfected (negative control), transfected with 200 ng EGFP reporter plasmid alone (positive control), or reporter plasmid+RNA duplexes at varying concentrations as described in Example 3.

HEK 293 cells were mock transfected (negative control), transfected with 200 ng EGFP reporter plasmid alone (positive control), or reporter plasmid+RNA duplexes at varying concentrations as described previously. EGFP expression was assessed using the FACS assay at 24 h post-transfection. Results are shown in FIG. 4. At 10 nM concentration, the traditional 21-mer siRNA duplex with 2-base 3'-overhangs targeted to Site-2 in the EGFP gene (SEQ ID Nos. 44/45) did not detectably reduce EGFP expression. In contrast, a 10 nM concentration of the longer 27-mer duplex RNA (SEQ ID No. 46/47) reduced EGFP by about 80% or more and 10 nM of a related 27-mer (SEQ ID No. 48/49) reduced EGFP by about 90% or more. As in Example 2 above, 3'- or 5'-overhangs did not improve activity over the blunt ended version. The 27-mer with the 2-base mismatch in the sense strand (SEQ ID Nos. 48/49) showed improved activity as compared to the perfectly matched 27-mer (SEQ ID Nos. 46/47). It is possible that destabilization of the RNA duplex at this position improves efficiency of cleavage by Dicer.

This example demonstrates that dsRNAs of the invention can efficiently target sites within the EGFP gene that were previously considered poor targets by previously known methods. Use of the method of the invention will therefore simplify site selection and design criteria for RNAi. This example also shows that the intentional placement of mismatches at the 3'-terminus of the sense strand increases the potency of the 27-mer duplex.

EXAMPLE 4

This example demonstrates the use of the disclosed dsRNA duplexes to reduce expression of the human HNRPH1 gene in HEK 293 cells.

Western Blot.

HEK 293 cells were cultured in a 6-well plate. At 30% confluence, cells were transfected with iRNA duplexes as outlined in Example 2 above except that all reagents were used at 5-fold higher volume due to the larger scale of the cultures. Cells were harvested at 72 h in 300 µl phosphate buffered saline (PBS) and sonicated for 10 sec. Cell lysates was centrifuged for 2 min at 14,000 g and the supernatant was collected. Aliquots of 2 µl were taken from the cleared lysates which were run on a 10% SDS-PAGE gel. The HNRPH1 gene product was detected using a rabbit polyclonal anti-HNRPH1 antiserum and an anti-rabbit antibody conjugated with alkaline phosphatase (Sigma, St. Louis, Mo.). As control, β-actin was detected by a murine anti-human actin antibody (Sigma, St. Louis, Mo.) and anti-mouse antibody conjugated with alkaline phosphatase (Sigma, St. Louis, Mo.), as previously described (Markovtsov et al., 2000, *Mol. Cell Biol.,* 20:7463-79).

Nucleic Acid Reagents.

The coding sequence of *Homo sapiens* heterogeneous nuclear ribonucleoprotein H1 (HNRPH1) mRNA is shown (Genbank accession No. NM_005520) below. The ATG start codon and TAA stop codons are highlighted in bold font and site target by siRNA reagents is underscored.

```
SEQ ID No. 50:
ttttttttttcgtcttagccacgcagaagtcgcgtgtctagtttgtttcgacgccggaccgcgtaagagacgatgat gtgggcacggaaggtggagagggattcgtggtgaaggtccggggcttgccctggtcttgctcggccgatgaagtgc agaggttttttctgactgcaaaattcaaaatggggctcaaggtattcgtttcatctacaccagagaaggcagacca agtggcgaggcttttgttgaacttgaatcagaagatgaagtcaaattggccctgaaaaaagacagagaaactatggg acacagatatgttgaagtattcaagtcaaacaacgttgaaatggattgggtgttgaagcatactggtccaaatagtc ctgacacggccaatgatggctttgtacggcttagaggacttcccttggatgtagcaaggaagaaattgttcagttc ttctcagggttggaaatcgtgccaaatgggataacattgccggtggacttccaggggaggagtacggggaggcctt cgtgcagtttgcttcacaggaaatagctgaaaaggctctaaagaaacacaaggaaagaatagggcacaggtatattg aaatctttaagagcagtagagctgaagttagaactcattatgatccaccacgaaagcttatggccatgcagcggcca ggtccttatgacagacctggggctggtagagggtataacagcattggcagaggagctggctttgagaggatgaggcg tggtgcttatggtggaggctatggaggctatgatgattacaatggctataatgatggctatggatttgggtcagata gatttggaagagacctcaattactgttttcaggaatgtctgatcacagatacggggatggtggctctactttccag
```

-continued
```
agcacaacaggacactgtgtacacatgcggggattaccttacagagctactgagaatgacatttataatttttttc accgctcaaccctgtgagagtacacattgaaattggtcctgatggcagagtaactggtgaagcagatgtcgagttcg caactcatgaagatgctgtggcagctatgtcaaaagacaaagcaaatatgcaacacagatatgtagaactcttcttg aattctacagcaggagcaagcggtggtgcttacgaacacagatatgtagaactcttcttgaattctacagcaggagc aagcggtggtgcttatggtagccaaatgatgggaggcatgggcttgtcaaaccagtccagctacgggggcccagcca gccagcagctgagtgggggttacggaggcggctacggtggccagagcagcatgagtggatacgaccaagttttacag gaaaactccagtgattttcaatcaaacattgcataggtaaccaaggagcagtgaacagcagctactacagtagtgga agccgtgcatctatgggcgtgaacggaatgggagggttgtctagcatgtccagtatgagtggtggatggggaatgta attgatcgatcctgatcactgactcttggtcaaccttttttttttttttttctttaagaaaacttcagtttaac agtttctgcaatacaagcttgtgatttatgcttactctaagtggaaatcaggattgttatgaagacttaaggcccag tattttgaatacaatactcatctaggatgtaacagtgaagctgagtaaactataactgttaaacttaagttccagc ttttctcaagttagttataggatgtacttaagcagtaagcgtatttaggtaaaagcagttgaattatgttaaatgtt gcccttgccacgttaaattgaacactgttttggatgcatgttgaaagacatgcttttatttttttgtaaaacaat ataggagctgtgtctactattaaaagtgaaacattttggcatgtttgttaattctagtttcatttaataacctgtaa ggcacgtaagtttaagcttttttttttttaagttaatgggaaaaatttgagacgcaataccaatacttaggatttt ggtcttggtgtttgtatgaaattctgaggccttgatttaaatctttcattgtattgtgatttccttttaggtatatt gcgctaagtgaaacttgtcaaataaatcctccttttaaaaactgc
```

RNA duplexes were synthesized and prepared as described in Example 1. RNA duplexes targeting HNRPH1 are summarized in Table 3 below.

TABLE 3

Summary of Oligonucleotide Reagents, HNRPH1 Site-1

| Sequence | Name | SEQ ID No. |
|---|---|---|
| 5' UGAACUUGAAUCAGAAGAUGAAGUCAAAUUGGC 3' | HNRPH1 Site-1 | SEQ ID NO: 69 |
| 5' CUUGAAUCAGAAGAUGAAGUU<br>3' UUGAACUUAGUCUUCUACUUC | HNRPH1-21 + 2 | SEQ ID No. 51<br>SEQ ID No. 52 |
| 5' AACUUGAAUCAGAAGAUGAAGUCAAAU<br>3' UUGAACUUAGUCUUCUACUUCAGUUUA | HNRPH1-27 + 0 | SEQ ID No. 53<br>SEQ ID No. 54 |

Figure 5:
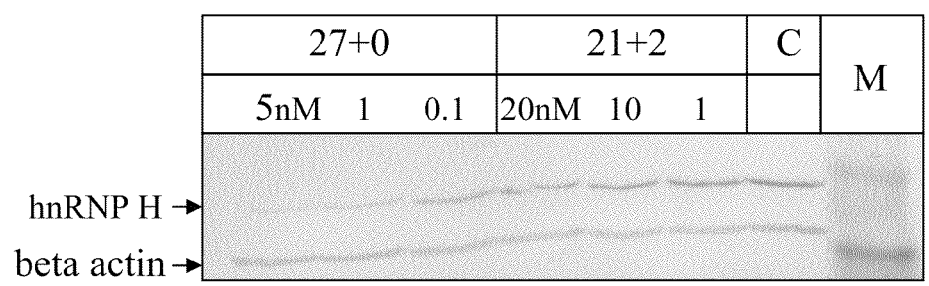
FIG. 5 shows superior knockout of the HNRPH1 gene by a 27-mer of the invention as compared to a 21-mer directed to the same target. Western blots obtained from HEK 293 cells after transfection with EGFP-specific siRNA (SEQ ID No. 6/7; C) (negative control) and an HNRPH1 specific 21-mer siRNA duplex (SEQ ID Nos. 51/52; 21+2) at varying concentrations, or with an HNRPH1 specific 27-mer siRNA duplex (SEQ ID Nos. 53/54; 27+0) at varying concentrations, as described in Example 4.

HEK 293 cells were transfected with EGFP-specific siRNA (SEQ ID No. 6/7) (negative control) and an HNRPH1 specific 21-mer siRNA duplex (SEQ ID Nos. 51/52) at varying concentrations, or with an HNRPH1 specific 27-mer siRNA duplex (SEQ ID Nos. 53/54) at varying concentrations, as described previously. HNRPH1 expression was assessed by Western Blot assay at 72 h post-transfection. Results are shown in FIG. 5. As shown, only a slight decrease in HNRPH1 protein levels occurred after treatment with 20 nM of the 21-mer siRNA (SEQ ID Nos 51/52) while significant inhibition was seen using 1 nM of the 27-mer dsRNA (SEQ ID Nos 53/54) and almost complete elimination of HNRPH1 protein was achieved using 5 nM of the 27-mer RNA duplex. Improved reduction in gene expression by RNAi methods is therefore also seen for human genes using the method of the invention.

EXAMPLE 5

This example demonstrates a method for determining whether a dsRNA serves as s substrate for Dicer.

In Vitro Dicer Assay.

Recombinant human Dicer enzyme (Gene Therapy Systems, San Diego, Calif.) was incubated with synthetic duplex RNA oligonucleotides according to the manufacturer's instructions. Briefly, 2 units of Dicer was incubated in a buffer supplied by the manufacturer with 250 pmoles of RNA duplex in a 50 µl volume (5 µM RNA concentration) for 18 h at 37° C. Half of each reaction was separated on non-denaturing PAGE (10% acrylamide) and visualized using ethidium bromide staining with UV excitation.

Results.

Figure 6:
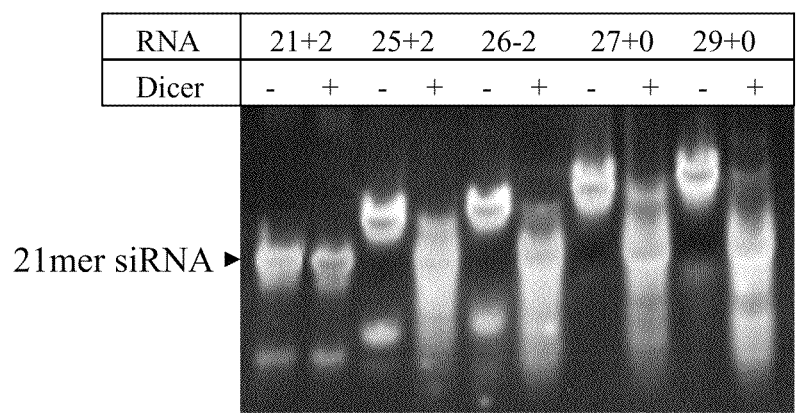
FIG. 6 shows the reaction of Dicer with various length RNA duplexes as described in Example 5. Dicer was able to digest 25-29-mers primarily into about a 21 basepair duplex but dd not digest the 21 nucleotide long test duplex.

RNA duplexes tested included 21-mer (SEQ ID No. 6/7), 25-mer (SEQ ID No. 18/19), 26-mer (SEQ ID No. 24/25), 27-mer (SEQ ID No. 30/31), and 29-mer (SEQ ID No. 40/41). The duplexes were subjected to Dicer digestion in vitro and visualized by PAGE. Results are shown in FIG. 6. As shown, the 21-mer RNA duplex did not react with Dicer. The 25-mer, 26-mer, 27-mer, and 29-mer duplexes all reacted with Dicer and were digested to a 21-mer size product, predominantly.

This example shows that the longer RNA duplexes used in the method of the invention are substrates for the Dicer endoribonuclease.

EXAMPLE 6

This example demonstrates that 27-mer duplexes have more RNAi activity than any of the shorter 21-mer duplexes that they encompass.

Theoretically, a variety of short 21-mer siRNAs could result from the action of Dicer on longer duplex RNAs. For example, based upon the antisense strand, 7 different 21-mer species could result from degradation of a 27-mer sequence. It is possible that one of these 21-mers (or a combination of 21-mers) accounts for the activity observed with the previously tested 27-mer dsRNA. This example shows that no single 21-mer duplex or mixture of 21-mers resulting from degradation of a 27-mer sequence functions as effectively as its parent 27-mer duplex at reducing EGFP expression.

Nucleic Acid Reagents.

RNA duplexes were prepared as described in Example 1. The sequences of a set of 21-mer RNA duplexes from within EGFP Site-1 were prepared. The duplexes are listed below in Table 4. The 21-mer duplexes are aligned beneath the parent 27-mer to illustrate their relative positioning. The 27-mer blunt duplex (SEQ ID No. 28/29) and the 21-mer duplex 21+2(7) (SEQ ID No. 6/7) are shown in Example 2 (Table 1) and were also used.

Figure 8:
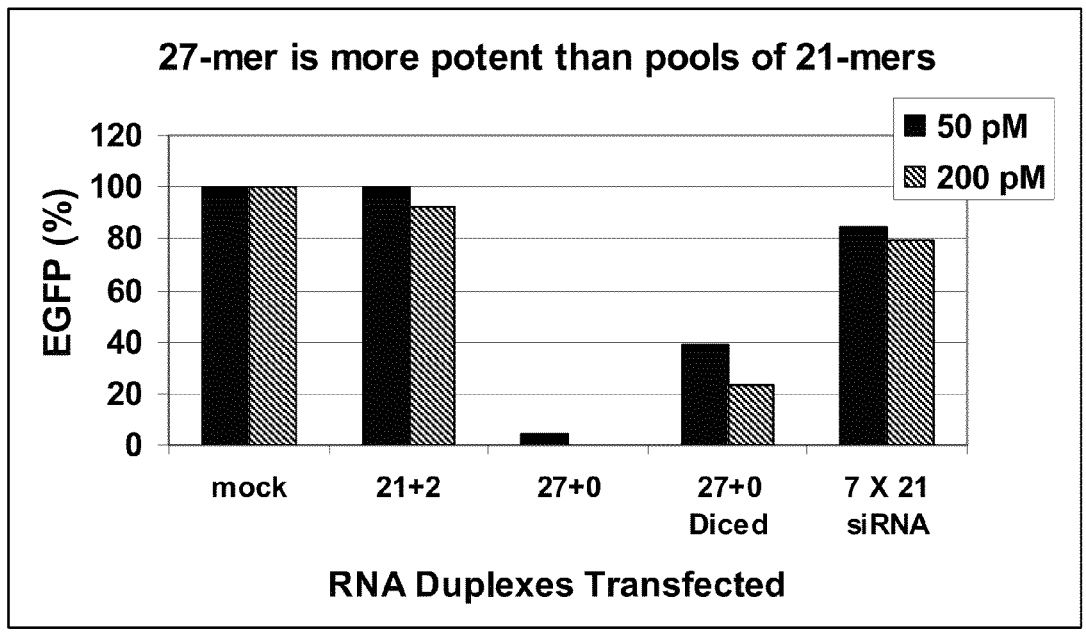
FIG. 8 shows the results of RNAi assays after treatment by various effector dsRNA molecules and pools of molecules as set forth in Example 6.

The activity of "diced" products made from digestion of the 27-mer duplex with recombinant Dicer enzyme in vitro was compared with the parent 27-mer compound in RNAi assays. The 27-mer duplex (SEQ ID No. 28/29) was degraded using Dicer as described in Example 5 above and fragments ("diced" products) were diluted and directly used in transfection experiments. EGFP expression levels were measured following transfection of HEK 293 cells with 200 ng EGFP reporter plasmid with a 21-mer duplex (SEQ ID No. 6/7), a 27-mer duplex (SEQ ID No. 28/29), products of in vitro Dicer degradation ("diced" products), a mutant 27-mer with 4 base central mismatch (SEQ ID No. 36/37), and the pooled set of 7 21-mer duplexes (SEQ ID Nos. 6/7 and 55/56, 57/58, 59/60, 61/62, 63/64, 65/66). Results are shown in FIG. 8. Again, the 27-mer duplex was the most potent reagent in reducing EGFP expression. The "diced" products were more effective than the set of pooled 21-mer duplexes. One explanation for this result is that the in vitro dicing reaction was incomplete and some intact 27-mer remains even after 18 h incubation (residual 27-mer is seen in FIG. 6).

This example provides another demonstration that the improved potency of dsRNA 27-mers is not derived from a highly active individual or a pooled set of short 21-mer duplexes.

TABLE 4

Summary of Oligonucleotide Reagents, EGFP Site-1, Tiled Set

| Sequence | Name | SEQ ID No. |
|---|---|---|
| 5' GCAAGCUGACCCUGAAGUUCAUCUGCACCACCGGCAAGC 3' | EGFP Site-1 | SEQ ID NO: 67 |
| 5' AAGCUGACCCUGAAGUUCAUCUGCACC<br>3' UUCGACUGGGACUUCAAGUAGACGUGG | EGFPS1-27 + 0 | SEQ ID No. 28<br>SEQ ID No. 29 |
| 5' CCUGAAGUUCAUCUGCACCAC<br>3' UGGGACUUCAAGUAGACGUGG | EGFPS1-21 + 2(1) | SEQ ID No. 55<br>SEQ ID No. 56 |
| 5' CCCUGAAGUUCAUCUGCACCA<br>3' CUGGGACUUCAAGUAGACGUG | EGFPS1-21 + 2(2) | SEQ ID No. 57<br>SEQ ID No. 58 |
| 5' ACCCUGAAGUUCAUCUGCACC<br>3' ACUGGGACUUCAAGUAGACGU | EGFPS1-21 + 2(3) | SEQ ID No. 59<br>SEQ ID No. 60 |
| 5' GACCCUGAAGUUCAUCUGCAC<br>3' GACUGGGACUUCAAGUAGACG | EGFPS1-21 + 2(4) | SEQ ID No. 61<br>SEQ ID No. 62 |
| 5' UGACCCUGAAGUUCAUCUGCA<br>3' CGACUGGGACUUCAAGUAGAC | EGFPS1-21 + 2(5) | SEQ ID No. 63<br>SEQ ID No. 64 |
| 5' CUGACCCUGAAGUUCAUCUGC<br>3' UCGACUGGGACUUCAAGUAGA | EGFES1-21 + 2(6) | SEQ ID No. 65<br>SEQ ID No. 66 |
| 5' GCUGACCCUGAAGUUCAUCUG<br>3' UUCGACUGGGACUUCAAGUAG | EGFES1-21 + 2(7) | SEQ ID No. 6<br>SEQ ID No. 7 |

Figure 7:
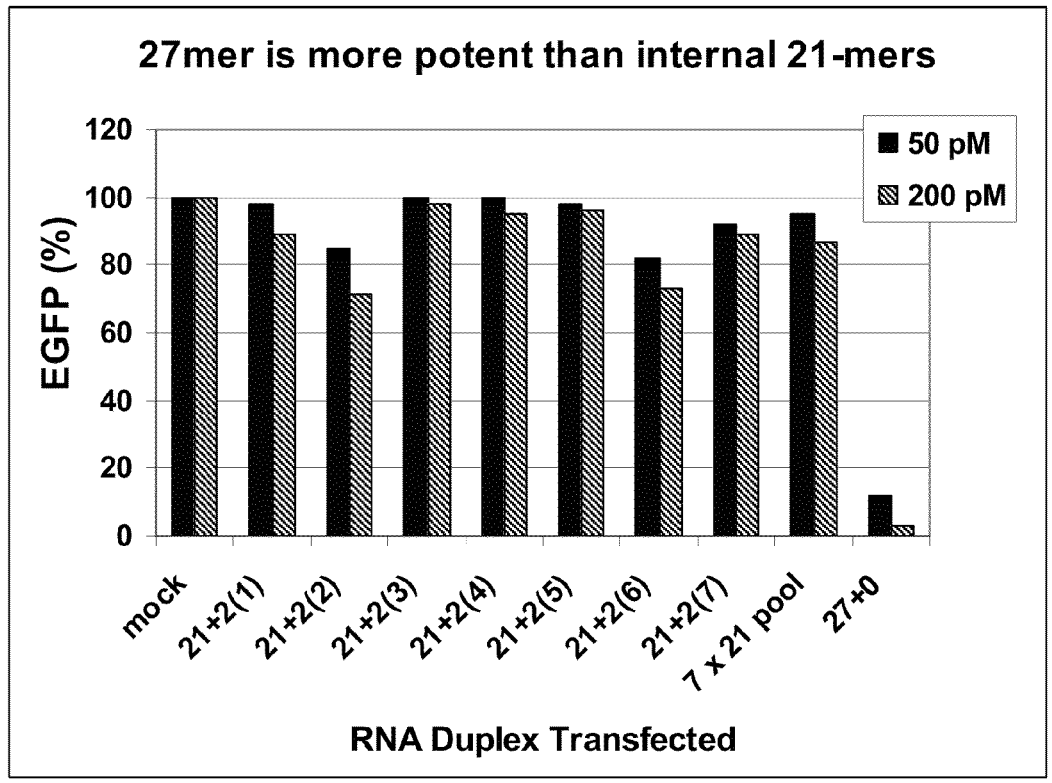
FIG. 7 shows the relative expression of EGFP after RNAi assays using a 27-mer dsRNA versus shorter 21-mer siRNAs contained within the 27-mer sequence as described in more detail in Example 6. As shown a blunt ended 27-mer that covers a poor site for a 21 nucleotide RNAi can effectively target that site.

The each of the 21-mer duplexes from Table 4 was transfected individually or together as a pool into HEK 293 cells with 200 ng of EGFP reporter plasmid as described previously. The result from each transfection was compared with the 27-mer duplex (SEQ ID No. 28/29). The relative EGFP expression from each experiment is shown in FIG. 7. At concentrations of 50 or 200 pM, none of the individual 21-mer duplexes or the pooled set of 7 21-mer duplexes showed activity comparable with the 27-mer duplex. For pools, 50 pM and 200 pM represent the total concentration of all RNAs transfected together, rather than for individual duplexes. FIG. 7 shows that the potency of the 27-mer duplex was much higher than for any of the shorter 21-mer sequences, which included every possible 21-mer duplex that could result from degradation of the parent 27-mer.

EXAMPLE 7

This example demonstrates that gene suppression using the 27-mer duplexes of the invention last twice as long as suppression achieved using 21-mer duplexes.

Suppression of gene expression using synthetic siRNA typically has a duration of 3-4 days in tissue culture (Chiu and Rana, 2002, *Mol. Cell*, 10:549-561). Methods that increase the duration of the RNAi effect would improve the functional utility of RNAi as an experimental tool in tissue culture and would be beneficial for use of RNAi in vivo.

Figure 9:
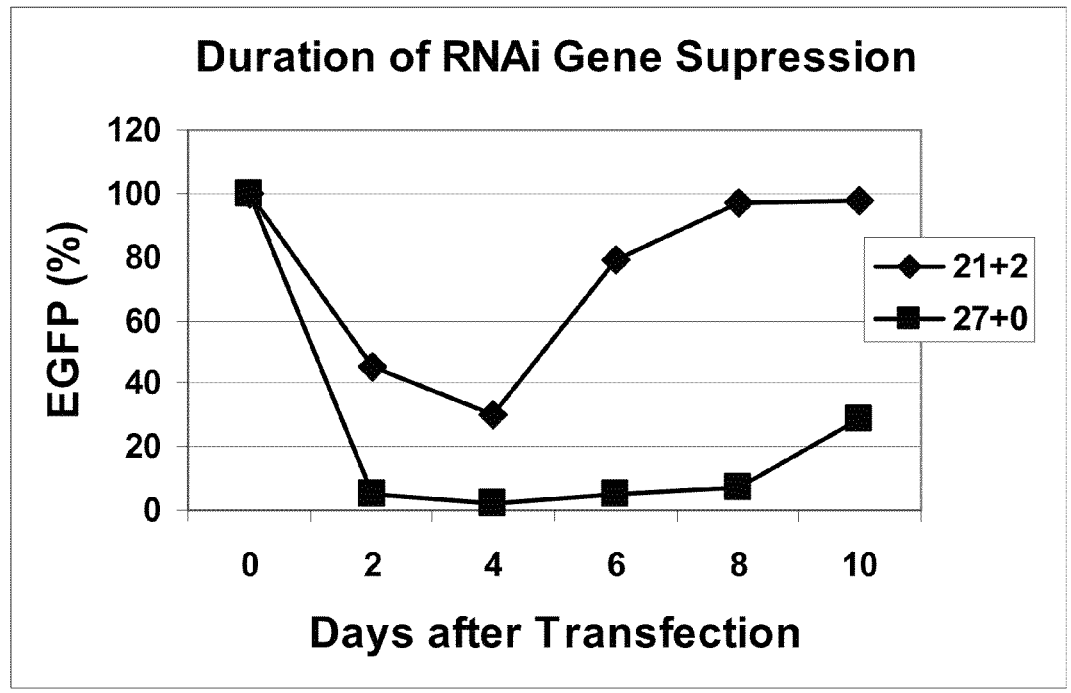
FIG. 9 shows the time course study of the duration of the RNAi effect with various effector molecules as described in Example 7. The study shows the duration of the RNAi effect is at least about twice as long with the 27-mer dsRNA of the invention as with 21-mers. The "27+0 UU" sequences are set forth in SEQ ID NOs:28 and 29. The "Mut-16" sequences are set forth in SEQ ID NOs:70 and 71. The "Mut-16,17" sequences are set forth in SEQ ID NOs:72 and 73. The "Mut-15,16,17" sequences are set forth in SEQ ID NOs:74 and 75.
Figure 10:
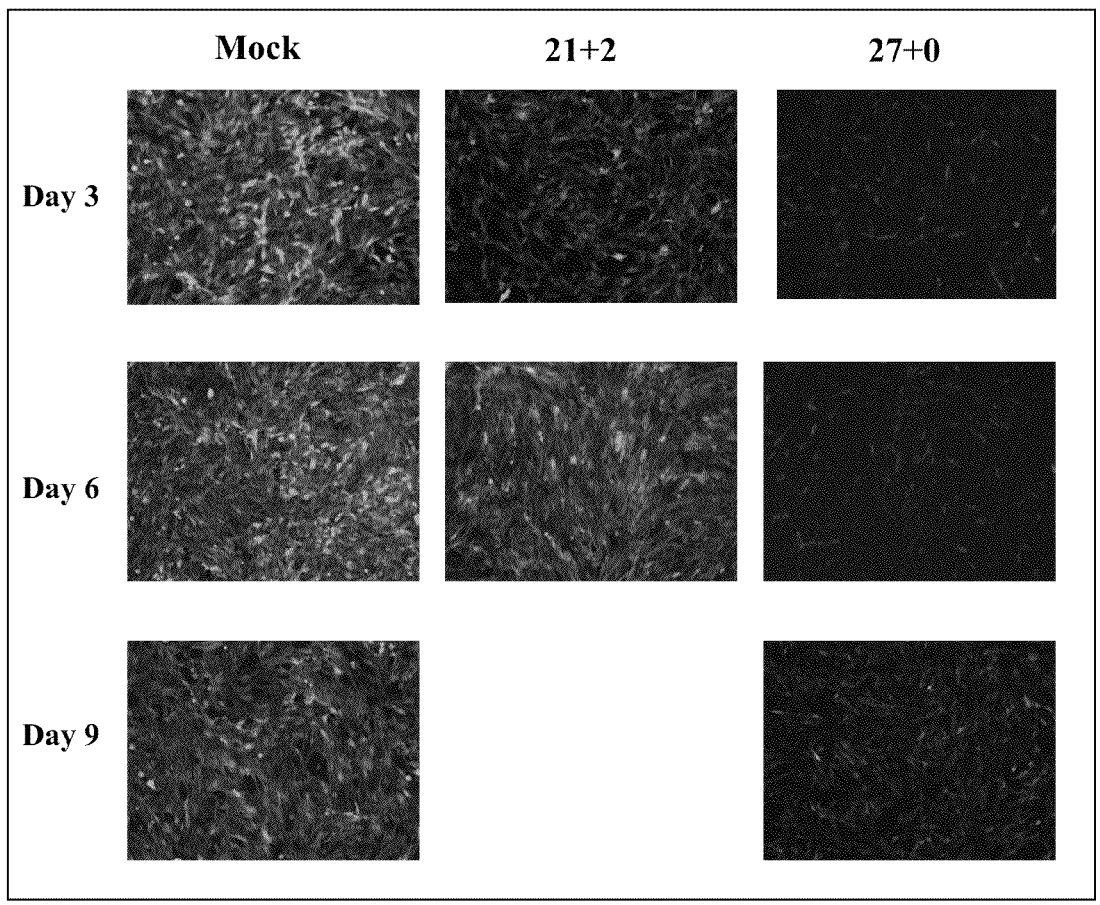
FIG. 10 shows the images of cells in a time course study of the duration of the RNAi effect with various effector molecules as described in Example 7. The study shows the duration of the RNAi effect is at least about twice as long with the 27-mer dsRNA of the invention as with 21-mers.

NIH 3T3 cells were transfected with 5 nM of either the 21-mer duplex (SEQ ID No. 6/7) or the 27-mer duplex (SEQ ID No. 30/31). Cell extracts were prepared and measured for EGFP protein expression in a cuvette fluorometer (as described in Example 2 above) at 2, 4, 6, 8, and 10 days post-transfection. Results are shown in FIG. 9. In addition, images of cells that were transfected in parallel using 1 nM siRNAs were obtained using fluorescence microscopy (as described in Example 2) and the images are shown in FIG. 10. EGFP expression was suppressed to about 70% of control levels at day 4 but returned to about 80% of control levels at day 6 and was at control levels at day 8. In contrast, suppression using the 27-mer duplex was about 90% or more at day 8 and was still at about 70% on day 10.

The 27-mer duplexes used in the present example demonstrates suppression of gene expression for at least twice the duration seen using 21-mer duplexes.

EXAMPLE 8

This example demonstrates that the dsRNA duplexes of the invention do not activate the interferon response.

Historically, long double stranded RNA was considered to be ineffective as an agent for reducing gene expression in mammalian cells because it tends to activate interferon pathway responses and lead to a variety of metabolic disturbances in cells which are not sequence specific. Short 21-mer siRNAs were considered useful for RNA I experiments because, in addition to suppressing gene expression, they avoid interferon activation. Because the more active double stranded RNAs of this invention are longer than known siRNA duplexes, they were examined further to show that they do not activate interferon. Duplexes of up to about 30-mer lengths were tested.

Interferon and PKR Assays.

HEK 293 cells were transfected with 20 nM T7 ssRNA (Kim et al., 2004, *Nat. Biotechnol.*, 22:321-325), 21-mer RNA duplex (SEQ ID No. 6/7), or 27-mer RNA duplex (SEQ ID No. 30/31) as described in Example 2 above. Culture medium was collected at 24 h and subjected to interferon alpha and beta ELISA assays (Research Diagnostics, Inc., Flanders, N.J.) according to the manufacturer's instructions, as previously described (Kim et al., 2004, *Nat. Biotechnol.*, 22:321-325).

Human double-stranded RNA (dsRNA)-dependent protein kinase (PKR) was assayed using the PKR activation assay (Gunnery et al., 1998, *Methods*, 15:189-98) in HEK 293 cell extracts. HEK 293 cells were transfected as described in Example 2 with 20 nM of each RNA and extracts were prepared 18 h post-transfection.

Results.

Figure 11:
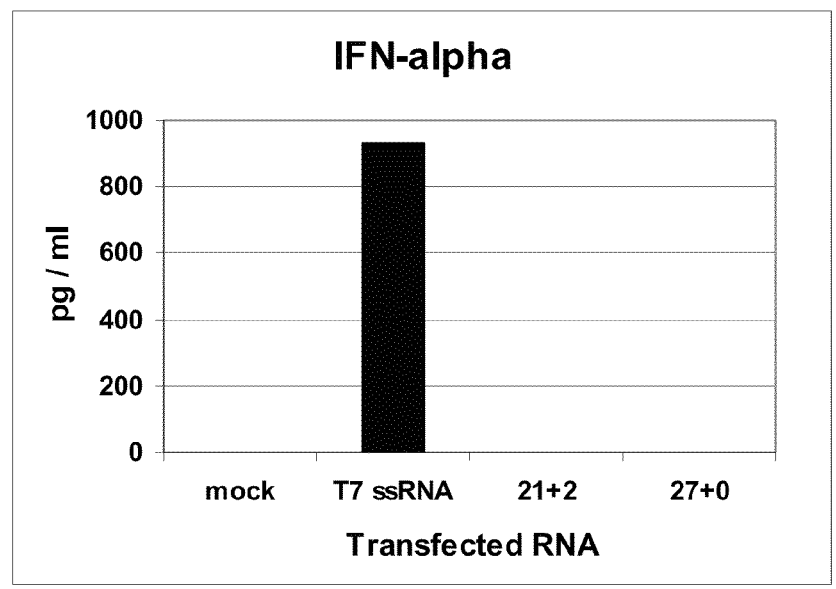
FIG. 11 shows that neither interferon alpha (FIG. 11A) or interferon beta (FIG. 11B) are induced by the 27-mer dsRNA of the invention as described in more detail in Example 8.
Figure 11:
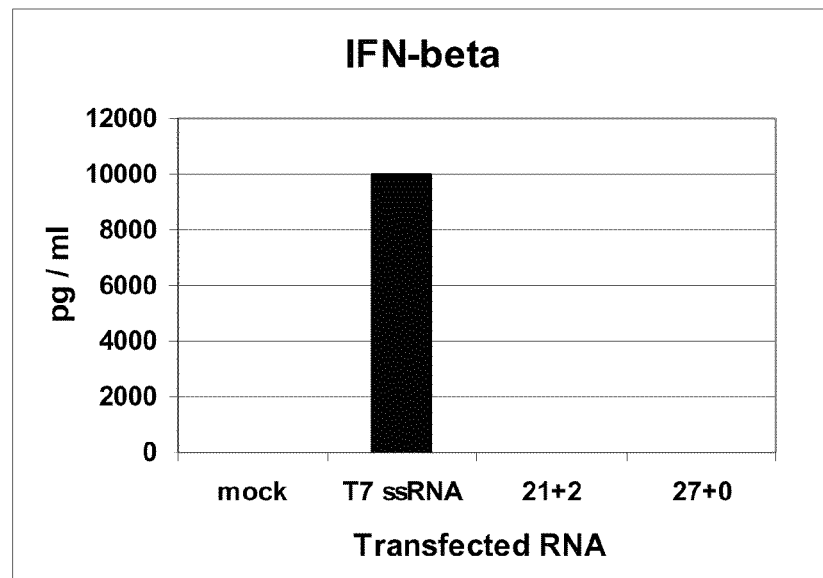

HEK 293 cells were transfected with ssRNA, 21-mer duplex, 27-mer duplex, or no RNA (negative control, mock transfection) as described above. As shown in FIG. 11, high levels of interferon alpha (FIG. 11A) and interferon beta (FIG. 11B) were detected after transfection with ssRNA however no interferon was detected when 21-mer or 27-mer RNAs were transfected.

Figure 12:
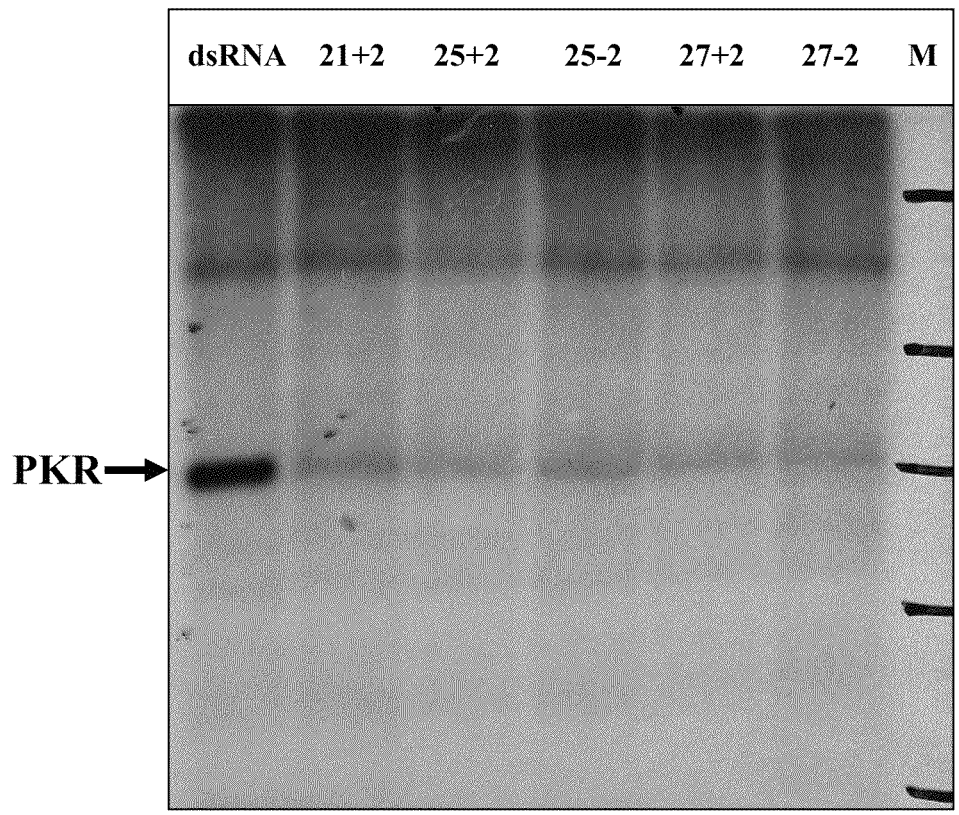
FIG. 12 shows the results of a PKR activation assay in which long dsRNA resulted in strong PKR activation (positive control) while all of the short synthetic RNAs showed no evidence for PKR activation.

HEK 293 cells were transfected with 400 bp EGFP dsRNA (at 20 nM), or 20 nM of chemically synthesized short RNA duplexes including 21+2 (SEQ ID No. 6/7), 25+2 (SEQ ID No. 18/19), 25-2 (SEQ ID No. 16/17), 27+2 (SEQ ID No. 34/35), and 27-2 (SEQ ID No. 32/33). Results of the PKR activation assay are shown in FIG. 12. The long dsRNA resulted in strong PKR activation (positive control) while all of the short synthetic RNAs showed no evidence for PKR activation.

We conclude that the longer synthetic RNAs used in the invention for improved RNAi mediated suppression of gene expression do not activate interferon responses and therefore should be usable in a wide variety of mammalian systems.

EXAMPLE 9

This example demonstrates a method for determining an effective dose of the dsRNA of the invention in a mammal A therapeutically effective amount of a composition containing a sequence that encodes a dsRNA, (i.e., an effective dosage), is an amount that inhibits expression of the product of the target gene by at least 10 percent. Higher percentages of inhibition, e.g., 20, 50, 90 95, 99 percent or higher may be preferred in certain circumstances. Exemplary doses include milligram or microgram amounts of the molecule per kilogram of subject or sample weight (e.g., about 1 microgram per kilogram to about 5 milligrams per kilogram, about 100 micrograms per kilogram to about 0.5 milligrams per kilogram, or about 1 microgram per kilogram to about 50 micrograms per kilogram). The compositions can be administered one or more times per week for between about 1 to 10 weeks, e.g., between 2 to 8 weeks, or between about 3 to 7 weeks, or for about 4, 5, or 6 weeks, as deemed necessary by the attending physician. Treatment of a subject with a therapeutically effective amount of a composition can include a single treatment or a series of treatments.

Appropriate doses of a particular dsRNA composition depend upon the potency of the molecule with respect to the expression or activity to be modulated. One or more of these molecules can be administered to an animal, particularly a mammal, and especially humans, to modulate expression or activity of one or more target genes. A physician may, for example, prescribe a relatively low dose at first, subsequently increasing the dose until an appropriate response is obtained. In addition, it is understood that the specific dose level for any particular subject will depend upon a variety of other factors including the severity of the disease, previous treatment regimen, other diseases present, off-target effects of the active agent, age, body weight, general health, gender, and diet of the patient, the time of administration, the route of administration, the rate of excretion, any drug combination, and the degree of expression or activity to be modulated.

The efficacy of treatment can be monitored by measuring the amount of the target gene mRNA (e.g. using real time PCR) or the amount of product encoded by the target gene, such as by Western blot analysis. In addition, the attending physician can monitor the symptoms associated with the disease or disorder afflicting the patient and compare with those symptoms recorded prior to the initiation of treatment.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

REFERENCES

Amarzguioui et al., Tolerance for Mutation and Chemical Modifications in a siRNA, Nucleic Acids Research, 2003, Vol. 31, No. 2, 589-595.

Bernstein, E., Caudy, A. A., Hammond, S. M., and Hannon, G. J. (2001) Role for a bidentate ribonuclease in the initiation step of RNA interference. Nature, 409:363-366.

Braasch et al., RNA Interference in Mammalian Cells by Chemically-Modified RNA, Biochemistry, 2003, 42, 7967-7975.

Bridge et al., Induction of an Interferon Response by RNAi Vectors in Mammalian Cells, Nature Genetics, 2003, Vol. 34, No. 3, 263-264.

Caplen, N. J., Parrish, S., Imani, F., Fire, A., and Morgan, R. A. (2001) Specific inhibition of gene expression by small double-stranded RNAs in invertebrate and vertebrate systems. Proc. Natl. Acad. Sci. USA, 98:9742-9747.

Chang et al., Gene Expression from Both Intronless and Intron-Containing Rous Sarcoma Virus Clones is Specifically Inhibited by Anti-Sense RNA, Molecular and Cellular Biology, 1985, Vol. 5, No. 9, 2341-2348.

Check, RNA to the Rescue?, Nature, 2003, 425, 10-12.

CHIU et al., siRNA Function in RNAi: A Chemical Modification Analysis, RNA, 2003, 9:1034-1048.

Chiu, Y. L., and Rana, T. R. (2002) RNAi in human cells: basic structural and functional features of small interfering RNA. Mol. Cell, 10:549-561.

Czauderna et al., Structural Variations and Stabilising Modifications of Synthetic siRNAs in Mammalian Cells, Nucleic Acids Research, 2003, Vol. 31, No. 11, 2705-2716.

Damha, M. J., and Ogilvie, K. K. (1993) Oligoribonucleotide synthesis. The silyl-phosphoramidite method. Methods Mol. Biol. 20:81-114.

Donbrow (Ed.) Microcapsules and nanoparticles in medicine and pharmacy. CRC Press, Boca Raton, Fla., pp. 125-14.

Elbashir et al., Functional Anatomy of siRNAs for Mediating Efficient RNAi in Drosophila melanogaster Embryo Lysate, EMBO Journal, 2001, Vol. 20, No. 33, 6877-6888.

Elbashir et al., RNA Interference is Mediated by 21- and 22-Nucleotide RNAs, Genes & Development, 2001, 15:188-200.

Elbashir, S. M., Harborth, J., Lendeckel, W., Yalcin, A., Weber, K., and Tuschl, T. (2001) Duplexes of 21-nucleotide RNAs mediate RNA interference in cultured mammalian cells. Nature, 411:494-498.

Elbashir, S. M., Lendeckel, W., and Tuschl, T. (2001) RNA interference is mediated by 21- and 22-nucleotide RNAs. Genes & Dev., 15:188-200.

Fire, A., Xu, S., Montgomery, M. K., Kostas, S. A., Driver, S. E., and Mellow, C. C. (1998) Potent and specific genetic interference by double-stranded RNA in Caenorhabditis elegans. Nature. 391:806-811.

Graessmann, M., Michaels, G., Berg, B., and Graessmann, A. (1991) Inhibition of SV40 gene expression by microinjected small antisense RNA and DNA molecules. Nucleic Acids Res. 19:53-59.

Gunnery, S., and Mathews, M. B. (1998) RNA binding and modulation of PKR activity. Methods, 15:189-98.

Hamada et al., Effects on RNA Interference in Gene Expression (RNAi) in Cultured Mammalian Cells of Mismatches and the Introduction of Chemical Modifications at the 3'-Ends of siRNAs, Antisense and Nucleic Acid Drug Development, 2002, 12:301-309

Hannon, RNA Interference, Nature, 2002, 418, 244-251.

Harborth, J., Elbashir, S. M., Vandenburgh, K., Manning a, H., Scaringe, S. A., Weber, K., and Tuschl, T. (2003) Sequence, chemical, and structural variation of small interfering RNAs and short hairpin RNAs and the effect on mammalian gene silencing. Antisense Nucleic Acid Drug Dev., 13:83-105.

Hohjoh, J. (2002) RNA interference (RNAi) induction with various types of synthetic oligonucleotide duplexes in cultured human cells. FEBS Lett., 521:195-199.

Holen, T., Amarzguioui, M., Wilger, M. T., Babaie, E., and Prydz, H. (2002) Positional effects of short interfering RNAs targeting the human coagulation trigger tissue factor. Nucleic Acids Res., 30:1757-1766.

Ji, J., Wernli, M., Klimkait, T., and Erb, P. (2003) Enhanced gene silencing by the application of multiple specific small interfering RNAs. FEBS Lett., 552:247-252.

Khvorova, A., Reynolds, A., and Jayasena, S. D. (2003) Functional siRNAs and miRNAs exhibit strand bias. Cell, 115: 209-216.

Kim, D. H., and Rossi, J. J. (2003) Coupling of RNAi-mediated target downregulation with gene replacement. Antisense Nucleic Acid Drug Dev., 13:151-155.

Kim, D. H., Longo, M., Han, Y., Lundberg, P., Cantin, E., and Rossi, J. J. (2004) Interferon induction by siRNAs and ssRNAs synthesized by phage polymerase. Nat. Biotechnol., 22:321-325.

Kretshmer-Kazemi Far et al., The Activity of siRNA in Mammalian Cells is Related to Structural Target Accessibility: A Comparison with Antisense Oligonucleotides, Nucleic Acids Research, 2003, Vol. 31, No. 15, 4417-4424.

Liu et al., R2D2, a Bridge Between the Initiator and Effector Steps of the Drosophila RNAi Pathway, Science, 2003, Vol. 301, 1921-1925.

Manche, L., Green, S. R., Schmedt, C., and Mathews, M. B. (1992) Interactions between double-stranded RNA regulators and the protein kinase DAI. Mol. Cell. Biol. 12:5238-5248.

Markovtsov, V., Nikolic, J. M., Goldman, J. A., Turck, C. W., Chou, M. Y., and Black, D. L. (2000) Cooperative assembly of an hnRNP complex induced by a tissue specific homolog of polypyrimidine tract binding protein. Mol. Cell Biol., 20:7463-79.

Martinez, J., Patkaniowska, A., Urlaub, H., Luhrmann, R., and Tuschl, T. (2002) Single-stranded antisense siRNAs guide target RNA cleavage in RNAi. Cell, 110:563-574.

McManus et al., Gene Silencing in Mammals by Small Interfering RNAs, Nature Reviews Genetics, 2002, Vol. 3, 737-747.

Melton, D. A. (1985) Injected anti-sense RNAs specifically block messenger RNA translation in vivo. Proc. Natl. Acad. Sci. USA. 82:144-148.

Minks, M. A., West, D. K., Benvin, S., and Baglioni, C. (1979) Structural requirements of double-stranded RNA for the activation of the 2'-5'-oligo(A) polymerase and protein kinase of interferon-treated HeLa cells. J. Biol. Chem. 254:10180-10183.

Napoli, C., Lemieux, C., and Jorgensen, R. (1990) Introduction of a chimeric chalcone synthase gene into petunia results in reversible co-suppression of homologous genes in trans. Plant Cell. 2:279-289.

Ngo et al., Double-Stranded RNA Induces mRNA Degradation in *Trypanosoma brucei*, Proceedings of the National Academy of Sciences of the United States of America, 1998, Vol. 95, 14687-14692.

Parrish, S., Fleenor, J., Xu, S., Mello, C., and Fire, A. (2000) Functional anatomy of a dsRNA trigger: differential requirements for the two trigger strands in RNA interference. Mol. Cell, 6:1077-1087.

Pellino et al., R2D2 Leads the Silencing Trigger to mRNA's Death Star, Cell, 2003, 115:132-133.

Reynolds et al., Rational siRNA Design for RNA Interference, Nature Biotechnology, 2004, 22, 1-5.

Reynolds, A., Leake, D., Boese, Q., Scaringe, S., Marshall, W. S., and Khvorova, A. (2004) Rational siRNA design for RNA interference. Nat. Biotechnol. 22:326-330.

Romano, N., and Macino, G. (1992) Quelling: transient inactivation of gene expression in *Neurospora crassa* by transformation with homologous sequences. Mol Microbiol. 6:3343-53.

Rossi, presentation at Integrated DNA Technologies, 2003.

Scherer et al., Approaches for the Sequence-Specific Knockdown of mRNA, Nature Biotechnology, 2003, Vol. 21, No. 12, 1457-1465.

Schwarz, D. S., Hutvagner, G., Du, T., Xu, Z., Aronin, N., and Zamore, P. D. (2003) Asymmetry in the assembly of the RNAi enzyme complex. Cell, 115:199-208.

Skipper, Elegant Tour de Force, Nature Reviews Genetics, 2003, Vol. 4, 79-80.

Sledz et al., Activation of the Interferon System by Short-Interfering RNAs, Nature Cell Biology, 2003, Vol. 5, No. 9, 834-839.

Stark, G. R., Kerr, I. M., Williams, B. R., Silverman, R. H., and Schreiber, R. D. (1998) How cells respond to interferons. Annu. Rev. Biochem. 67:227-264.

Tuschl, T., Zamore, P. D., Lehmann, R., Bartel, D. P., and Sharp, P. A. (1999) Targeted mRNA degradation by double-stranded RNA in vitro. Genes & Dev., 13:3191-3197.

Ui-Tei, K., Naito, Y., Takahashi, F., Haraguchi, T., Ohki-Hamazaki, H., Juni, A., Ueda, R., and Saigo, K. (2004) Guidelines for the selection of highly effective siRNA sequences for mammalian and chick RNA interference. Nucleic Acids Res., 32:936-948.

Waterhouse et al., Exploring Plant Genomes by RNA-Induced Gene Silencing, Nature Reviews Genetics, 2003, Vol. 4, 29-38.

Wincott, F., DiRenzo, A., Shaffer, C., Grimm, S., Tracz, D., Workman, C., Sweedler, D., Gonzalez, C., Scaringe, S., and Usman, N. (1995) Synthesis, deprotection, analysis and purification of RNA and ribozymes. Nucleic Acids Res., 23:2677-84.

Xu et al., Effective Small Interfering RNAs and Phosphorothioate Antisense DNAs Have Different Preferences for Target Sites in the Luciferase mRNAs, Biochemical and Biophysical Research Communications, 2003, 306, 712-717.

Zamore, P. D., Tuschl, T., Sharp, P. A., and Bartel, D. P. (2000) RNAi: double-stranded RNA directs the ATP-dependent cleavage of mRNA at 21 to 23 nucleotide intervals. Cell, 101:25-33.

What is claimed is:

1. A method for reducing expression of a target gene in a mammalian cell comprising: contacting a cell in vitro with an isolated double stranded nucleic acid in an amount sufficient to reduce expression of a target gene in said cell, wherein said double stranded nucleic acid comprises a first oligonucleotide strand comprising ribonucleotides and having a 5' terminus and a 3' terminus and a second oligonucleotide strand comprising ribonucleotides and having a 5' terminus and a 3' terminus and wherein said double stranded nucleic acid comprises blunt ends, wherein each of said first and said second strands consists of the same number of nucleotide residues and is 25-30 nucleotides, wherein the ultimate and penultimate residues of said 3' terminus of said first strand and the ultimate and penultimate residues of said 5' terminus of said second strand form one or two mismatched base pairs, and wherein said second oligonucleotide strand is sufficiently complementary to a target mRNA along at least 19 nucleotides of said second oligonucleotide strand length to reduce target gene expression when said double stranded nucleic acid is introduced into a mammalian cell, thereby reducing expression of the target gene in said mammalian cell.

2. The method of claim 1, wherein each of said first and said second strands has a length which is at least 26 and at most 30 nucleotides.

3. The method of claim 1, wherein said isolated double stranded nucleic acid is a double stranded RNA and wherein said double stranded RNA is cleaved endogenously in said cell by Dicer.

4. The method of claim 3, wherein the cleavage facilitates incorporation of the second oligonucleotide strand into RISC.

5. The method of claim 1, wherein the amount of said isolated double stranded nucleic acid sufficient to reduce expression of the target gene is selected from the group consisting of 1 nanomolar or less, 200 picomolar or less, and 50 picomolar or less in the environment of said cell.

6. The method of claim 1, wherein target gene expression is reduced by an amount (expressed by %) selected from the group consisting of at least 10%, at least 50% and at least 80-90%.

7. The method of claim 1, wherein each of said first and said second strands has a length of 27 nucleotides.

8. The method of claim 5, wherein each of said first and said second strands has a length which is at least 26 and at most 30 nucleotides.

9. The method of claim 5, wherein each of said first and said second strands has a length of 27 nucleotides.

10. A method for reducing expression of a target gene in a mammal comprising: administering an isolated double stranded nucleic acid to a mammal in an amount sufficient to reduce expression of a target gene in the mammal, wherein said double stranded nucleic acid comprises a first oligonucleotide strand comprising ribonucleotides and having a 5' terminus and a 3' terminus and a second oligonucleotide strand comprising ribonucleotides and having a 5' terminus and a 3' terminus and wherein said double stranded nucleic acid comprises blunt ends, wherein each of said first and said second strands consists of the same number of nucleotide residues and is 25-30 nucleotides, wherein the ultimate and penultimate residues of said 3' terminus of said first strand and the ultimate and penultimate residues of said 5' terminus of said second strand form one or two mismatched base pairs, and wherein said second oligonucleotide strand is sufficiently complementary to a target mRNA along at least 19 nucleotides of said second oligonucleotide strand length to reduce target gene expression when said double stranded nucleic acid is introduced into a mammalian cell, thereby reducing expression of the target gene in the mammal.

11. The method of claim 10, wherein said isolated double stranded nucleic acid is administered at a dosage selected from the group consisting of 1 microgram to 5 milligrams per kilogram of said mammal per day, 100 micrograms to 0.5 milligrams per kilogram of said mammal per day, 0.001 to 0.25 milligrams per kilogram of said mammal per day, 0.01 to 20 micrograms per kilogram of said mammal per day, 0.01 to 10 micrograms per kilogram of said mammal per day, 0.10 to 5 micrograms per kilogram of said mammal per day, and 0.1 to 2.5 micrograms per kilogram of said mammal per day.

12. The method of claim 10, wherein said administering step comprises a mode selected from the group consisting of intravenous injection, intramuscular injection, intraperitoneal injection, infusion, subcutaneous injection, transdermal, aerosol, rectal, vaginal, topical, oral and inhaled delivery.

13. The method of claim 10, wherein each of said first and said second strands has a length which is at least 26 and at most 30 nucleotides.

14. The method of claim 10, wherein each of said first and said second strands has a length of 27 nucleotides.

15. The method of claim 11, wherein each of said first and said second strands has a length which is at least 26 and at most 30 nucleotides.

16. The method of claim 11, wherein each of said first and said second strands has a length of 27 nucleotides.

17. The method of claim 10, wherein said isolated double stranded nucleic acid is a double stranded RNA and wherein said double stranded RNA is cleaved endogenously in said cell by Dicer.

18. The method of claim 17, wherein the cleavage facilitates incorporation of the second oligonucleotide strand into RISC.

19. A formulation comprising an isolated double stranded nucleic acid, wherein said isolated double stranded nucleic acid comprises a first oligonucleotide strand comprising ribonucleotides and having a 5' terminus and a 3' terminus and a second oligonucleotide strand comprising ribonucleotides and having a 5' terminus and a 3' terminus and wherein said double stranded nucleic acid comprises blunt ends, wherein each of said first and said second strands consists of the same number of nucleotide residues and is 25-30 nucleotides, wherein the ultimate and penultimate residues of said 3' terminus of said first strand and the ultimate and penultimate residues of said 5' terminus of said second strand form one or two mismatched base pairs, and wherein said second oligonucleotide strand is sufficiently complementary to a target mRNA along at least 19 nucleotides of said second oligonucleotide strand length to reduce target gene expression when said double stranded nucleic acid is introduced into a mammalian cell, wherein said double stranded nucleic acid is present in an amount effective to reduce target gene expression when said double stranded nucleic acid is introduced into a mammalian cell in vitro by an amount (expressed by %) selected from the group consisting of at least 10%, at least 50% and at least 80-90%.

20. The formulation of claim 19, wherein said effective amount is selected from the group consisting of 1 nanomolar or less, 200 picomolar or less, and 50 picomolar or less in the environment of said cell.

21. A formulation comprising an isolated double stranded nucleic acid, wherein said isolated double stranded nucleic acid comprises a first oligonucleotide strand comprising ribonucleotides and having a 5' terminus and a 3' terminus and a second oligonucleotide strand comprising ribonucleotides and having a 5' terminus and a 3' terminus and wherein said double stranded nucleic acid comprises blunt ends, wherein each of said first and said second strands consists of the same number of nucleotide residues and is 25-30 nucleotides, wherein the ultimate and penultimate residues of said 3' terminus of said first strand and the ultimate and penultimate residues of said 5' terminus of said second strand form one or two mismatched base pairs, and wherein said second oligonucleotide strand is sufficiently complementary to a target mRNA along at least 19 nucleotides of said second oligonucleotide strand length to reduce target gene expression when said double stranded nucleic acid is introduced into a mammalian cell, wherein said double stranded nucleic acid is present in an amount effective to reduce target gene expression when said double stranded nucleic acid is introduced into a cell of a mammalian subject by an amount (expressed by %) selected from the group consisting of at least 10%, at least 50% and at least 80-90%.

22. The formulation of claim 21, wherein said effective amount is a dosage selected from the group consisting of 1 microgram to 5 milligrams per kilogram of said subject per day, 100 micrograms to 0.5 milligrams per kilogram of said subject per day, 0.001 to 0.25 milligrams per kilogram of said subject per day, 0.01 to 20 micrograms per kilogram of said subject per day, 0.01 to 10 micrograms per kilogram of said subject per day, 0.10 to 5 micrograms per kilogram of said subject per day, and 0.10 to 2.5 micrograms per kilogram of said subject per day.

23. A mammalian cell containing an isolated double stranded nucleic acid, wherein said isolated double stranded nucleic acid comprises a first oligonucleotide strand comprising ribonucleotides and having a 5' terminus and a 3' terminus and a second oligonucleotide strand comprising ribonucleotides and having a 5' terminus and a 3' terminus and wherein said double stranded nucleic acid comprises blunt ends, wherein each of said first and said second strands consists of the same number of nucleotide residues and is 25-30 nucleotides, wherein the ultimate and penultimate residues of said 3' terminus of said first strand and the ultimate and penultimate residues of said 5' terminus of said second strand form one or two mismatched base pairs, and wherein said second oligonucleotide strand is sufficiently complementary to a target mRNA along at least 19 nucleotides of said second oligonucleotide strand length to reduce target gene expression when said double stranded nucleic acid is introduced into a mammalian cell.

* * * * *

UNITED STATES PATENT AND TRADEMARK OFFICE
CERTIFICATE OF CORRECTION

| | | |
|---|---|---|
| PATENT NO. | : 9,365,849 B2 | |
| APPLICATION NO. | : 14/019911 | |
| DATED | : June 14, 2016 | |
| INVENTOR(S) | : John J. Rossi et al. | |

It is certified that error appears in the above-identified patent and that said Letters Patent is hereby corrected as shown below:

In the Specification

Column 1, Lines 22-25:
"This invention was made in part with Government support under Grant Numbers AI29329 and HL074704 awarded by the National Institute of Health. The Government has certain rights in this invention."

Should be:
-- This invention was made with government support under HL074704, and AI029329 awarded by the National Institutes of Health. The government has certain rights in the invention. --

Signed and Sealed this
Second Day of January, 2024

Katherine Kelly Vidal
Director of the United States Patent and Trademark Office

SEQUENCE LISTING

```
<160> NUMBER OF SEQ ID NOS: 75

<210> SEQ ID NO 1
<211> LENGTH: 720
<212> TYPE: DNA
<213> ORGANISM: Artificial
<220> FEATURE:
<223> OTHER INFORMATION: EGFP from cloning vector pEGFP-C1

<400> SEQUENCE: 1
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
```

```
gaccactacc agcagaacac ccccatcggc gacggccccg tgctgctgcc cgacaaccac    600
tacctgagca cccagtccgc cctgagcaaa gaccccaacg agaagcgcga tcacatggtc    660
ctgctggagt tcgtgaccgc cgccgggatc actctcggca tggacgagct gtacaagtaa    720
```

<210> SEQ ID NO 2
<211> LENGTH: 21
<212> TYPE: RNA
<213> ORGANISM: Artificial
<220> FEATURE:
<223> OTHER INFORMATION: siRNA
<400> SEQUENCE: 2

```
gcaagcugac ccugaaguuc a                                               21
```

<210> SEQ ID NO 3
<211> LENGTH: 21
<212> TYPE: RNA
<213> ORGANISM: Artificial
<220> FEATURE:
<223> OTHER INFORMATION: siRNA
<400> SEQUENCE: 3

```
gaugaacuuc aggucagcu u                                                21
```

<210> SEQ ID NO 4
<211> LENGTH: 21
<212> TYPE: RNA
<213> ORGANISM: Artificial
<220> FEATURE:
<223> OTHER INFORMATION: siRNA
<400> SEQUENCE: 4

```
aagcugaccc ugaaguucau c                                               21
```

<210> SEQ ID NO 5
<211> LENGTH: 21
<212> TYPE: RNA
<213> ORGANISM: Artificial
<220> FEATURE:
<223> OTHER INFORMATION: siRNA
<400> SEQUENCE: 5

```
gaugaacuuc aggucagcu u                                                21
```

<210> SEQ ID NO 6
<211> LENGTH: 21
<212> TYPE: RNA
<213> ORGANISM: Artificial
<220> FEATURE:
<223> OTHER INFORMATION: siRNA
<400> SEQUENCE: 6

```
gcugacccug aaguucaucu g                                               21
```

<210> SEQ ID NO 7
<211> LENGTH: 21
<212> TYPE: RNA
<213> ORGANISM: Artificial
<220> FEATURE:
<223> OTHER INFORMATION: siRNA
<400> SEQUENCE: 7

```
gaugaacuuc aggucagcu u                                                21
```

<210> SEQ ID NO 8
<211> LENGTH: 23
<212> TYPE: RNA
<213> ORGANISM: Artificial
<220> FEATURE:
<223> OTHER INFORMATION: siRNA

<400> SEQUENCE: 8
gcaagcugac ccugaaguuc auu                                                 23

<210> SEQ ID NO 9
<211> LENGTH: 23
<212> TYPE: RNA
<213> ORGANISM: Artificial
<220> FEATURE:
<223> OTHER INFORMATION: siRNA

<400> SEQUENCE: 9
cagaugaacu ucaggucag cuu                                                  23

<210> SEQ ID NO 10
<211> LENGTH: 24
<212> TYPE: RNA
<213> ORGANISM: Artificial
<220> FEATURE:
<223> OTHER INFORMATION: siRNA

<400> SEQUENCE: 10
gcugacccug aaguucaucu gcuu                                                24

<210> SEQ ID NO 11
<211> LENGTH: 24
<212> TYPE: RNA
<213> ORGANISM: Artificial
<220> FEATURE:
<223> OTHER INFORMATION: siRNA

<400> SEQUENCE: 11
gcagaugaac uucaggguca gcuu                                                24

<210> SEQ ID NO 12
<211> LENGTH: 24
<212> TYPE: RNA
<213> ORGANISM: Artificial
<220> FEATURE:
<223> OTHER INFORMATION: siRNA

<400> SEQUENCE: 12
gcaagcugac ccugaaguuc auuu                                                24

<210> SEQ ID NO 13
<211> LENGTH: 24
<212> TYPE: RNA
<213> ORGANISM: Artificial
<220> FEATURE:
<223> OTHER INFORMATION: siRNA

<400> SEQUENCE: 13
gcagaugaac uucaggguca gcuu                                                24

<210> SEQ ID NO 14
<211> LENGTH: 24
<212> TYPE: RNA
<213> ORGANISM: Artificial
<220> FEATURE:
<223> OTHER INFORMATION: siRNA

```
<400> SEQUENCE: 14
gcugacccug aaguucaucu gcuu                                          24

<210> SEQ ID NO 15
<211> LENGTH: 24
<212> TYPE: RNA
<213> ORGANISM: Artificial
<220> FEATURE:
<223> OTHER INFORMATION: siRNA

<400> SEQUENCE: 15
gcagaugaac uucaggguca gcuu                                          24

<210> SEQ ID NO 16
<211> LENGTH: 25
<212> TYPE: RNA
<213> ORGANISM: Artificial
<220> FEATURE:
<223> OTHER INFORMATION: siRNA

<400> SEQUENCE: 16
gcaagcugac ccugaaguuc aucuu                                         25

<210> SEQ ID NO 17
<211> LENGTH: 25
<212> TYPE: RNA
<213> ORGANISM: Artificial
<220> FEATURE:
<223> OTHER INFORMATION: siRNA

<400> SEQUENCE: 17
ugcagaugaa cuucaggguc agcuu                                         25

<210> SEQ ID NO 18
<211> LENGTH: 25
<212> TYPE: RNA
<213> ORGANISM: Artificial
<220> FEATURE:
<223> OTHER INFORMATION: siRNA

<400> SEQUENCE: 18
gcugacccug aaguucaucu gcauu                                         25

<210> SEQ ID NO 19
<211> LENGTH: 25
<212> TYPE: RNA
<213> ORGANISM: Artificial
<220> FEATURE:
<223> OTHER INFORMATION: siRNA

<400> SEQUENCE: 19
ugcagaugaa cuucaggguc agcuu                                         25

<210> SEQ ID NO 20
<211> LENGTH: 26
<212> TYPE: RNA
<213> ORGANISM: Artificial
<220> FEATURE:
<223> OTHER INFORMATION: siRNA

<400> SEQUENCE: 20
aagcugaccc ugaaguucau cugcac                                        26

<210> SEQ ID NO 21
```

```
<211> LENGTH: 26
<212> TYPE: RNA
<213> ORGANISM: Artificial
<220> FEATURE:
<223> OTHER INFORMATION: siRNA

<400> SEQUENCE: 21
gugcagauga acuucagggu cagcuu                                              26

<210> SEQ ID NO 22
<211> LENGTH: 26
<212> TYPE: RNA
<213> ORGANISM: Artificial
<220> FEATURE:
<223> OTHER INFORMATION: siRNA

<400> SEQUENCE: 22
aagcugaccc ugaaguucau cugcuu                                              26

<210> SEQ ID NO 23
<211> LENGTH: 26
<212> TYPE: RNA
<213> ORGANISM: Artificial
<220> FEATURE:
<223> OTHER INFORMATION: siRNA

<400> SEQUENCE: 23
gugcagauga acuucagggu cagcuu                                              26

<210> SEQ ID NO 24
<211> LENGTH: 26
<212> TYPE: RNA
<213> ORGANISM: Artificial
<220> FEATURE:
<223> OTHER INFORMATION: siRNA

<400> SEQUENCE: 24
gcaagcugac ccugaaguuc aucuuu                                              26

<210> SEQ ID NO 25
<211> LENGTH: 26
<212> TYPE: RNA
<213> ORGANISM: Artificial
<220> FEATURE:
<223> OTHER INFORMATION: siRNA

<400> SEQUENCE: 25
gugcagauga acuucagggu cagcuu                                              26

<210> SEQ ID NO 26
<211> LENGTH: 26
<212> TYPE: RNA
<213> ORGANISM: Artificial
<220> FEATURE:
<223> OTHER INFORMATION: siRNA

<400> SEQUENCE: 26
gcugacccug aaguucaucu gcacuu                                              26

<210> SEQ ID NO 27
<211> LENGTH: 26
<212> TYPE: RNA
<213> ORGANISM: Artificial
<220> FEATURE:
<223> OTHER INFORMATION: siRNA

<400> SEQUENCE: 27
```

-continued

```
gugcagauga acuucagggu cagcuu                                              26

<210> SEQ ID NO 28
<211> LENGTH: 27
<212> TYPE: RNA
<213> ORGANISM: Artificial
<220> FEATURE:
<223> OTHER INFORMATION: siRNA

<400> SEQUENCE: 28
aagcugaccc ugaaguucau cugcacc                                             27

<210> SEQ ID NO 29
<211> LENGTH: 27
<212> TYPE: RNA
<213> ORGANISM: Artificial
<220> FEATURE:
<223> OTHER INFORMATION: siRNA

<400> SEQUENCE: 29
ggugcagaug aacuucaggg ucagcuu                                             27

<210> SEQ ID NO 30
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_feature
<222> LOCATION: (1)..(1)
<223> OTHER INFORMATION: conjugated to 6-FAM

<400> SEQUENCE: 30
aagcugaccc ugaaguucau cugcauu                                             27

<210> SEQ ID NO 31
<211> LENGTH: 27
<212> TYPE: RNA
<213> ORGANISM: Artificial
<220> FEATURE:
<223> OTHER INFORMATION: siRNA
<220> FEATURE:
<221> NAME/KEY: misc_feature
<222> LOCATION: (1)..(1)
<223> OTHER INFORMATION: conjugated to 6-FAM

<400> SEQUENCE: 31
ggugcagaug aacuucaggg ucagcuu                                             27

<210> SEQ ID NO 32
<211> LENGTH: 27
<212> TYPE: RNA
<213> ORGANISM: Artificial
<220> FEATURE:
<223> OTHER INFORMATION: siRNA

<400> SEQUENCE: 32
gcugacccug aaguucaucu gcacauu                                             27

<210> SEQ ID NO 33
<211> LENGTH: 27
<212> TYPE: RNA
<213> ORGANISM: Artificial
<220> FEATURE:
<223> OTHER INFORMATION: siRNA
```

```
<400> SEQUENCE: 33
ggugcagaug aacuucaggg ucagcuu                                    27

<210> SEQ ID NO 34
<211> LENGTH: 27
<212> TYPE: RNA
<213> ORGANISM: Artificial
<220> FEATURE:
<223> OTHER INFORMATION: siRNA

<400> SEQUENCE: 34
gcugacccug aaguucaucu gcacauu                                    27

<210> SEQ ID NO 35
<211> LENGTH: 27
<212> TYPE: RNA
<213> ORGANISM: Artificial
<220> FEATURE:
<223> OTHER INFORMATION: siRNA

<400> SEQUENCE: 35
ggugcagaug aacuucaggg ucagcuu                                    27

<210> SEQ ID NO 36
<211> LENGTH: 27
<212> TYPE: RNA
<213> ORGANISM: Artificial
<220> FEATURE:
<223> OTHER INFORMATION: siRNA

<400> SEQUENCE: 36
aagcugaccc uguucaucau cugcacc                                    27

<210> SEQ ID NO 37
<211> LENGTH: 27
<212> TYPE: RNA
<213> ORGANISM: Artificial
<220> FEATURE:
<223> OTHER INFORMATION: siRNA

<400> SEQUENCE: 37
ggugcagaug augaacaggg ucagcuu                                    27

<210> SEQ ID NO 38
<211> LENGTH: 28
<212> TYPE: RNA
<213> ORGANISM: Artificial
<220> FEATURE:
<223> OTHER INFORMATION: siRNA

<400> SEQUENCE: 38
aagcugaccc ugaaguucau cugcacca                                   28

<210> SEQ ID NO 39
<211> LENGTH: 28
<212> TYPE: RNA
<213> ORGANISM: Artificial
<220> FEATURE:
<223> OTHER INFORMATION: siRNA

<400> SEQUENCE: 39
uggugcagau gaacuucagg gucagcuu                                   28

<210> SEQ ID NO 40
<211> LENGTH: 29
```

```
<212> TYPE: RNA
<213> ORGANISM: Artificial
<220> FEATURE:
<223> OTHER INFORMATION: siRNA

<400> SEQUENCE: 40
aagcugaccc ugaaguucau cugcaccac                                      29

<210> SEQ ID NO 41
<211> LENGTH: 29
<212> TYPE: RNA
<213> ORGANISM: Artificial
<220> FEATURE:
<223> OTHER INFORMATION: siRNA

<400> SEQUENCE: 41
guggugcaga ugaacuucag ggucagcuu                                      29

<210> SEQ ID NO 42
<211> LENGTH: 30
<212> TYPE: RNA
<213> ORGANISM: Artificial
<220> FEATURE:
<223> OTHER INFORMATION: siRNA

<400> SEQUENCE: 42
aagcugaccc ugaaguucau cugcaccacc                                     30

<210> SEQ ID NO 43
<211> LENGTH: 30
<212> TYPE: RNA
<213> ORGANISM: Artificial
<220> FEATURE:
<223> OTHER INFORMATION: siRNA

<400> SEQUENCE: 43
gguggugcag augaacuuca ggucagcuu                                      30

<210> SEQ ID NO 44
<211> LENGTH: 21
<212> TYPE: RNA
<213> ORGANISM: Artificial
<220> FEATURE:
<223> OTHER INFORMATION: siRNA

<400> SEQUENCE: 44
gcagcacgac uucuucaagu u                                              21

<210> SEQ ID NO 45
<211> LENGTH: 21
<212> TYPE: RNA
<213> ORGANISM: Artificial
<220> FEATURE:
<223> OTHER INFORMATION: siRNA

<400> SEQUENCE: 45
cuugaagaag ucgugcugcu u                                              21

<210> SEQ ID NO 46
<211> LENGTH: 27
<212> TYPE: RNA
<213> ORGANISM: Artificial
<220> FEATURE:
<223> OTHER INFORMATION: siRNA

<400> SEQUENCE: 46
```

```
aagcagcacg acuucuucaa guccgcc                                           27
```

<210> SEQ ID NO 47
<211> LENGTH: 27
<212> TYPE: RNA
<213> ORGANISM: Artificial
<220> FEATURE:
<223> OTHER INFORMATION: siRNA

<400> SEQUENCE: 47

```
ggcggacuug aagaagucgu gcugcuu                                           27
```

<210> SEQ ID NO 48
<211> LENGTH: 27
<212> TYPE: RNA
<213> ORGANISM: Artificial
<220> FEATURE:
<223> OTHER INFORMATION: siRNA

<400> SEQUENCE: 48

```
aagcagcacg acuucuucaa guccggg                                           27
```

<210> SEQ ID NO 49
<211> LENGTH: 27
<212> TYPE: RNA
<213> ORGANISM: Artificial
<220> FEATURE:
<223> OTHER INFORMATION: siRNA

<400> SEQUENCE: 49

```
ggcggacuug aagaagucgu gcugcuu                                           27
```

<210> SEQ ID NO 50
<211> LENGTH: 2201
<212> TYPE: DNA
<213> ORGANISM: Homo sapiens

<400> SEQUENCE: 50

```
tttttttttt cgtcttagcc acgcagaagt cgcgtgtcta gtttgtttcg acgccggacc        60
gcgtaagaga cgatgatgtt gggcacggaa ggtggagagg gattcgtggt gaaggtccgg       120
ggcttgccct ggtcttgctc ggccgatgaa gtgcagaggt ttttttctga ctgcaaaatt       180
caaaatgggg ctcaaggtat tcgtttcatc tacaccagag aaggcagacc aagtggcgag       240
gcttttgttg aacttgaatc agaagatgaa gtcaaattgg ccctgaaaaa agacagagaa       300
actatgggac acagatatgt tgaagtattc aagtcaaaca acgttgaaat ggattgggtg       360
ttgaagcata ctggtccaaa tagtcctgac acggccaatg atggctttgt acggcttaga       420
ggacttccct ttgatgtag caaggaagaa attgttcagt tcttctcagg gttggaaatc       480
gtgccaaatg ggataacatt gccggtggac ttccagggga ggagtacggg ggaggccttc       540
gtgcagtttg cttcacagga aatagctgaa aaggctctaa agaaacacaa ggaaagaata       600
gggcacaggt atattgaaat ctttaagagc agtagagctg aagttagaac tcattatgat       660
ccaccacgaa agcttatggc catgcagcgg ccaggtcctt atgacagacc tggggctggt       720
agagggtata acagcattgg cagaggagct ggctttgaga ggatgaggcg tggtgcttat       780
ggtggaggct atggaggcta tgatgattac aatggctata atgatggcta tggatttggg       840
tcagatagat ttggaagaga cctcaattac tgttttcag gaatgtctga tcacagatac       900
ggggatggtg gctctacttt ccagagcaca acaggacact gtgtacacat gcggggatta       960
ccttacagag ctactgagaa tgacattttt aattttttt caccgctcaa ccctgtgaga      1020
```

-continued

```
gtacacattg aaattggtcc tgatggcaga gtaactggtg aagcagatgt cgagttcgca      1080
actcatgaag atgctgtggc agctatgtca aaagacaaag caaatatgca acacagatat      1140
gtagaactct tcttgaattc tacagcagga gcaagcggtg gtgcttacga acacagatat      1200
gtagaactct tcttgaattc tacagcagga gcaagcggtg gtgcttatgg tagccaaatg      1260
atgggaggca tgggcttgtc aaaccagtcc agctacgggg gcccagccag ccagcagctg      1320
agtgggggtt acggaggcgg ctacggtggc cagagcagca tgagtggata cgaccaagtt      1380
ttacaggaaa actccagtga ttttcaatca acattgcat aggtaaccaa ggagcagtga       1440
acagcagcta ctacagtagt ggaagccgtg catctatggg cgtgaacgga atgggagggt      1500
tgtctagcat gtccagtatg agtggtggat ggggaatgta attgatcgat cctgatcact      1560
gactcttggt caacctttt ttttttttt ttttctttaa gaaaacttca gtttaacagt       1620
ttctgcaata caagcttgtg atttatgctt actctaagtg gaaatcagga ttgttatgaa      1680
gacttaaggc ccagtatttt tgaatacaat actcatctag gatgtaacag tgaagctgag      1740
taaactataa ctgttaaact taagttccag cttttctcaa gttagttata ggatgtactt      1800
aagcagtaag cgtatttagg taaaagcagt tgaattatgt taaatgttgc cctttgccac      1860
gttaaattga acactgtttt ggatgcatgt tgaaagacat gcttttatt tttttgtaaa       1920 acaatatagg agctgtgtct actattaaaa gtgaaacatt ttggcatgtt tgttaattct      1980
agtttcattt aataacctgt aaggcacgta agtttaagct ttttttttt ttaagttaat       2040 gggaaaaatt tgagacgcaa taccaatact taggattttg gtcttggtgt ttgtatgaaa      2100
ttctgaggcc ttgatttaaa tctttcattg tattgtgatt tccttttagg tatattgcgc      2160
taagtgaaac ttgtcaaata aatcctcctt ttaaaaactg c                          2201
```

<210> SEQ ID NO 51
<211> LENGTH: 21
<212> TYPE: RNA
<213> ORGANISM: Artificial
<220> FEATURE:
<223> OTHER INFORMATION: siRNA

<400> SEQUENCE: 51
cuugaaucag aagaugaagu u        21

<210> SEQ ID NO 52
<211> LENGTH: 21
<212> TYPE: RNA
<213> ORGANISM: Artificial
<220> FEATURE:
<223> OTHER INFORMATION: siRNA

<400> SEQUENCE: 52
cuucaucuuc ugauucaagu u        21

<210> SEQ ID NO 53
<211> LENGTH: 27
<212> TYPE: RNA
<213> ORGANISM: Artificial
<220> FEATURE:
<223> OTHER INFORMATION: siRNA

<400> SEQUENCE: 53
aacuugaauc agaagaugaa gucaaau   27

<210> SEQ ID NO 54

```
<211> LENGTH: 27
<212> TYPE: RNA
<213> ORGANISM: Artificial
<220> FEATURE:
<223> OTHER INFORMATION: siRNA

<400> SEQUENCE: 54
auuugacuuc aucuucugau ucaaguu                                          27

<210> SEQ ID NO 55
<211> LENGTH: 21
<212> TYPE: RNA
<213> ORGANISM: Artificial
<220> FEATURE:
<223> OTHER INFORMATION: siRNA

<400> SEQUENCE: 55
ccugaaguuc aucugcacca c                                                21

<210> SEQ ID NO 56
<211> LENGTH: 21
<212> TYPE: RNA
<213> ORGANISM: Artificial
<220> FEATURE:
<223> OTHER INFORMATION: siRNA

<400> SEQUENCE: 56
ggugcagaug aacuucaggg u                                                21

<210> SEQ ID NO 57
<211> LENGTH: 21
<212> TYPE: RNA
<213> ORGANISM: Artificial
<220> FEATURE:
<223> OTHER INFORMATION: siRNA

<400> SEQUENCE: 57
cccugaaguu caucugcacc a                                                21

<210> SEQ ID NO 58
<211> LENGTH: 21
<212> TYPE: RNA
<213> ORGANISM: Artificial
<220> FEATURE:
<223> OTHER INFORMATION: siRNA

<400> SEQUENCE: 58
gugcagauga acuucagggu c                                                21

<210> SEQ ID NO 59
<211> LENGTH: 21
<212> TYPE: RNA
<213> ORGANISM: Artificial
<220> FEATURE:
<223> OTHER INFORMATION: siRNA

<400> SEQUENCE: 59
acccugaagu ucaucugcac c                                                21

<210> SEQ ID NO 60
<211> LENGTH: 21
<212> TYPE: RNA
<213> ORGANISM: Artificial
<220> FEATURE:
<223> OTHER INFORMATION: siRNA

<400> SEQUENCE: 60
```

-continued ugcagaugaa cuucaggguc a    21

<210> SEQ ID NO 61
<211> LENGTH: 21
<212> TYPE: RNA
<213> ORGANISM: Artificial
<220> FEATURE:
<223> OTHER INFORMATION: siRNA

<400> SEQUENCE: 61
gacccugaag uucaucugca c    21

<210> SEQ ID NO 62
<211> LENGTH: 21
<212> TYPE: RNA
<213> ORGANISM: Artificial
<220> FEATURE:
<223> OTHER INFORMATION: siRNA

<400> SEQUENCE: 62
gcagaugaac uucaggguca g    21

<210> SEQ ID NO 63
<211> LENGTH: 21
<212> TYPE: RNA
<213> ORGANISM: Artificial
<220> FEATURE:
<223> OTHER INFORMATION: siRNA

<400> SEQUENCE: 63
ugacccugaa guucaucugc a    21

<210> SEQ ID NO 64
<211> LENGTH: 21
<212> TYPE: RNA
<213> ORGANISM: Artificial
<220> FEATURE:
<223> OTHER INFORMATION: siRNA

<400> SEQUENCE: 64
cagaugaacu ucaggucag c    21

<210> SEQ ID NO 65
<211> LENGTH: 21
<212> TYPE: RNA
<213> ORGANISM: Artificial
<220> FEATURE:
<223> OTHER INFORMATION: siRNA

<400> SEQUENCE: 65
cugacccuga aguucaucug c    21

<210> SEQ ID NO 66
<211> LENGTH: 21
<212> TYPE: RNA
<213> ORGANISM: Artificial
<220> FEATURE:
<223> OTHER INFORMATION: siRNA

<400> SEQUENCE: 66
agaugaacuu caggucagc u    21

<210> SEQ ID NO 67
<211> LENGTH: 39
<212> TYPE: RNA

```
<213> ORGANISM: Artificial
<220> FEATURE:
<223> OTHER INFORMATION: mRNA from EGFP from cloning vector pEGFP-C1

<400> SEQUENCE: 67
gcaagcugac ccugaaguuc aucugcacca ccggcaagc                              39

<210> SEQ ID NO 68
<211> LENGTH: 32
<212> TYPE: RNA
<213> ORGANISM: Artificial
<220> FEATURE:
<223> OTHER INFORMATION: mRNA of EGFP from cloning vector

<400> SEQUENCE: 68
ugaagcagca cgacuucuuc aaguccgcca ug                                     32

<210> SEQ ID NO 69
<211> LENGTH: 33
<212> TYPE: RNA
<213> ORGANISM: Homo sapiens

<400> SEQUENCE: 69
ugaacuugaa ucagaagaug aagucaaauu ggc                                    33

<210> SEQ ID NO 70
<211> LENGTH: 27
<212> TYPE: RNA
<213> ORGANISM: Artificial
<220> FEATURE:
<223> OTHER INFORMATION: siRNA

<400> SEQUENCE: 70
aagcugaccc ugaagaucau cugcauu                                           27

<210> SEQ ID NO 71
<211> LENGTH: 27
<212> TYPE: RNA
<213> ORGANISM: Artificial
<220> FEATURE:
<223> OTHER INFORMATION: siRNA

<400> SEQUENCE: 71
ggugcagaug aucuucaggg ucagcuu                                           27

<210> SEQ ID NO 72
<211> LENGTH: 27
<212> TYPE: RNA
<213> ORGANISM: Artificial
<220> FEATURE:
<223> OTHER INFORMATION: siRNA

<400> SEQUENCE: 72
aagcugaccc ugaagaacau cugcauu                                           27

<210> SEQ ID NO 73
<211> LENGTH: 27
<212> TYPE: RNA
<213> ORGANISM: Artificial
<220> FEATURE:
<223> OTHER INFORMATION: siRNA

<400> SEQUENCE: 73
ggugcagaug uucuucaggg ucagcuu                                           27
```

```
<210> SEQ ID NO 74
<211> LENGTH: 27
<212> TYPE: RNA
<213> ORGANISM: Artificial
<220> FEATURE:
<223> OTHER INFORMATION: siRNA

<400> SEQUENCE: 74
aagcugaccc ugaacaacau cugcauu                                          27

<210> SEQ ID NO 75
<211> LENGTH: 27
<212> TYPE: RNA
<213> ORGANISM: Artificial
<220> FEATURE:
<223> OTHER INFORMATION: siRNA

<400> SEQUENCE: 75
ggugcagaug uuguucaggg ucagcuu                                          27
```